US012653832B2

(12) United States Patent
Savage et al.

(10) Patent No.: US 12,653,832 B2
(45) **Date of Patent: *Jun. 16, 2026**

(54) METHODS FOR TREATING LUNG INFECTIONS AND INFLAMMATION

(71) Applicant: BRIGHAM YOUNG UNIVERSITY, Provo, UT (US)

(72) Inventors: Paul B. Savage, Mapleton, UT (US); Carl A. Genberg, Las Vegas, NV (US); Michael D. Triplett, New Albany, OH (US)

(73) Assignee: Brigham Young University, Provo, UT (US)

( * ) Notice: Subject to any disclaimer, the term of this patent is extended or adjusted under 35 U.S.C. 154(b) by 490 days.

This patent is subject to a terminal disclaimer.

(21) Appl. No.: 18/135,405

(22) Filed: Apr. 17, 2023

(65) Prior Publication Data

US 2023/0372362 A1 Nov. 23, 2023

Related U.S. Application Data

(63) Continuation of application No. 14/515,858, filed on Oct. 16, 2014, now Pat. No. 11,690,855.

(60) Provisional application No. 61/892,263, filed on Oct. 17, 2013.

(51) Int. Cl.

| | |
|---|---|
| ***A61K 31/575*** | (2006.01) |
| ***A61K 9/00*** | (2006.01) |
| ***A61K 31/427*** | (2006.01) |
| ***A61K 31/496*** | (2006.01) |
| ***A61K 31/7036*** | (2006.01) |
| ***A61K 31/7048*** | (2006.01) |
| ***A61K 31/7052*** | (2006.01) |
| ***A61K 38/06*** | (2006.01) |
| ***A61K 38/12*** | (2006.01) |
| ***A61K 38/14*** | (2006.01) |
| ***A61K 45/06*** | (2006.01) |

(52) U.S. Cl.

CPC .......... *A61K 31/575* (2013.01); *A61K 9/0078* (2013.01); *A61K 31/427* (2013.01); *A61K 31/496* (2013.01); *A61K 31/7036* (2013.01); *A61K 31/7048* (2013.01); *A61K 31/7052* (2013.01); *A61K 38/06* (2013.01); *A61K 38/12* (2013.01); *A61K 38/14* (2013.01); *A61K 45/06* (2013.01)

(58) Field of Classification Search

CPC .. A61K 31/575; A61K 9/0078; A61K 31/427; A61K 31/496; A61K 31/7036; A61K 31/7048; A61K 31/7052; A61K 38/06; A61K 38/12; A61K 38/14; A61K 45/06

See application file for complete search history.

(56) References Cited

U.S. PATENT DOCUMENTS

| | | | |
|---|---|---|---|
| 821,187 | A | 5/1906 | Peters |
| 3,843,779 | A | 10/1974 | Norfleet |
| 4,248,236 | A | 2/1981 | Linder |
| 4,284,236 | A | 8/1981 | Bradshaw |
| 4,289,755 | A | 9/1981 | Dhabhar |
| 4,296,206 | A | 10/1981 | Simons, Jr. |
| 4,473,988 | A | 10/1984 | Scott |
| 4,661,341 | A | 4/1987 | Benedict et al. |
| 4,723,950 | A | 2/1988 | Lee |
| 4,765,855 | A | 8/1988 | Geoffroy-Dechaume et al. |
| 4,842,593 | A | 6/1989 | Jordan et al. |
| 4,865,855 | A | 9/1989 | Hansen et al. |
| 4,972,848 | A | 11/1990 | Di et al. |
| 5,025,754 | A | 6/1991 | Plyler |
| 5,286,479 | A | 2/1994 | Garlich et al. |
| 5,310,545 | A | 5/1994 | Eisen |
| 5,352,682 | A | 10/1994 | Sipos |
| 5,356,630 | A | 10/1994 | Laurencin et al. |
| 5,364,650 | A | 11/1994 | Guthery |
| 5,380,839 | A | 1/1995 | McCall et al. |
| 5,552,057 | A | 9/1996 | Hughes et al. |
| 5,624,704 | A | 4/1997 | Darouiche et al. |
| 5,687,714 | A | 11/1997 | Kolobow et al. |
| 5,721,359 | A | 2/1998 | Dunn et al. |
| 5,763,430 | A | 6/1998 | Zasloff |
| 5,919,183 | A | 7/1999 | Field |
| 6,117,332 | A | 9/2000 | Hatch et al. |
| 6,143,738 | A | 11/2000 | Zasloff |
| 6,217,896 | B1 | 4/2001 | Benjamin |
| 6,224,622 | B1 | 5/2001 | Kotzev |
| 6,228,393 | B1 | 5/2001 | Dicosmo et al. |
| 6,329,488 | B1 | 12/2001 | Terry et al. |
| 6,344,184 | B1 | 2/2002 | Rolla |
| 6,350,738 | B1 | 2/2002 | Savage et al. |
| 6,486,148 | B2 | 11/2002 | Savage et al. |
| 6,562,318 | B1 | 5/2003 | Filler |
| 6,582,713 | B2 | 6/2003 | Newell et al. |
| 6,673,771 | B1 | 1/2004 | Greene et al. |
| 6,767,904 | B2 | 7/2004 | Savage et al. |

(Continued)

FOREIGN PATENT DOCUMENTS

| | | | |
|---|---|---|---|
| CA | 2322847 | A1 | 9/1999 |
| CA | 2640584 | A1 | 8/2007 |

(Continued)

OTHER PUBLICATIONS

U.S. Appl. filed Mar. 20, 2018, Savage., U.S. Appl. No. 15/926,534.

(Continued)

*Primary Examiner* — Andrew D Kosar
*Assistant Examiner* — Phillip Matthew Rzeczycki
(74) *Attorney, Agent, or Firm* — Workman Nydegger

(57) ABSTRACT

Methods of treating, reducing, or preventing lung infections and/or lung inflammation include identifying a patient in need of treatment and administering a therapeutically or prophylactically effective amount of at least one cationic steroid antimicrobial (CSA), or a pharmaceutically acceptable salt thereof. Treatment of cystic fibrosis lung infections, COPD lung infections, inflammation of the lungs in these patient populations, and lung scarring in these patient populations is also described.

38 Claims, 5 Drawing Sheets

(56) References Cited

U.S. PATENT DOCUMENTS

| | | | |
|---|---|---|---|
| 6,773,717 | B1 | 8/2004 | Winstrom |
| 6,803,030 | B2 | 10/2004 | De et al. |
| 6,803,066 | B2 | 10/2004 | Traeder et al. |
| 6,824,044 | B1 | 11/2004 | Apstun et al. |
| 6,872,303 | B2 | 3/2005 | Knapp et al. |
| 6,872,306 | B2 | 3/2005 | Shen |
| 6,939,376 | B2 | 9/2005 | Betts et al. |
| 7,226,577 | B2 | 6/2007 | Cappelletti et al. |
| 7,235,552 | B1 | 6/2007 | Hesse et al. |
| 7,282,214 | B2 | 10/2007 | Willcox et al. |
| 7,381,439 | B2 | 6/2008 | Hilgren et al. |
| 7,481,973 | B2 | 1/2009 | Beilfuss et al. |
| 7,598,234 | B2 | 10/2009 | Savage et al. |
| 7,611,692 | B2 | 11/2009 | Cappelletti et al. |
| 7,659,061 | B2 | 2/2010 | Hendl et al. |
| 7,754,705 | B2 | 7/2010 | Savage et al. |
| 7,850,947 | B2 | 12/2010 | Cappelletti et al. |
| 7,854,941 | B2 | 12/2010 | Urban et al. |
| 7,993,903 | B2 | 8/2011 | Hayakawa et al. |
| 7,999,390 | B2 | 8/2011 | Ishigaki et al. |
| 8,211,879 | B2 | 7/2012 | Savage et al. |
| 8,420,050 | B2 | 4/2013 | Cappelletti et al. |
| 8,444,954 | B2 | 5/2013 | Cappelletti et al. |
| 8,529,681 | B1 | 9/2013 | Hibbs et al. |
| 8,530,002 | B1 | 9/2013 | Hibbs et al. |
| 8,557,031 | B1 | 10/2013 | Hibbs et al. |
| 8,623,416 | B2 | 1/2014 | Zasloff |
| 8,691,252 | B2 | 4/2014 | Savage |
| 8,784,857 | B2 | 7/2014 | Savage |
| 8,787,857 | B2 | 7/2014 | Ezaki |
| 8,932,614 | B2 | 1/2015 | Savage et al. |
| 8,945,217 | B2 | 2/2015 | Savage et al. |
| 8,975,310 | B2 | 3/2015 | Savage |
| 9,155,746 | B2 | 10/2015 | Genberg et al. |
| 9,161,942 | B2 | 10/2015 | Genberg et al. |
| 9,180,132 | B2 | 11/2015 | Fein et al. |
| 9,314,472 | B2 | 4/2016 | Beus et al. |
| 9,345,655 | B2 | 5/2016 | Vazquez et al. |
| 9,387,215 | B2 | 7/2016 | Beus et al. |
| 9,434,759 | B1 | 9/2016 | Savage |
| 9,527,883 | B2 | 12/2016 | Savage et al. |
| 9,533,063 | B1 | 1/2017 | Savage |
| 9,546,195 | B2 | 1/2017 | Savage |
| 9,603,859 | B2 | 3/2017 | Genberg et al. |
| 10,226,550 | B2 | 3/2019 | Savage et al. |
| 10,441,595 | B2 | 10/2019 | Genberg et al. |
| 10,568,893 | B2 | 2/2020 | Savage et al. |
| 11,690,855 | B2 * | 7/2023 | Savage ................ A61K 31/427 514/169 |
| 12,097,212 | B2 * | 9/2024 | Savage .................. A01N 55/00 |
| 2002/0019376 | A1 | 2/2002 | Savage et al. |
| 2002/0091278 | A1 | 7/2002 | Savage et al. |
| 2002/0091433 | A1 | 7/2002 | Ding et al. |
| 2002/0115121 | A1 | 8/2002 | Garwin |
| 2003/0018306 | A1 | 1/2003 | Bucay-Couto et al. |
| 2003/0099717 | A1 | 5/2003 | Cabrera |
| 2003/0170354 | A1 | 9/2003 | Beelman et al. |
| 2003/0232791 | A1 | 12/2003 | Levitt et al. |
| 2004/0009227 | A1 | 1/2004 | Yao |
| 2004/0011358 | A1 | 1/2004 | Smaldone et al. |
| 2004/0018154 | A1 | 1/2004 | Pan et al. |
| 2004/0058974 | A1 | 3/2004 | Courtney et al. |
| 2004/0071781 | A1 | 4/2004 | Chattopadhyay et al. |
| 2004/0126409 | A1 | 7/2004 | Willcox et al. |
| 2004/0134292 | A1 | 7/2004 | Roth |
| 2004/0170563 | A1 | 9/2004 | Meade |
| 2004/0259445 | A1 | 12/2004 | Hilfenhaus et al. |
| 2005/0032765 | A1 | 2/2005 | Savage et al. |
| 2005/0075321 | A1 | 4/2005 | Ahlem et al. |
| 2005/0244468 | A1 | 11/2005 | Huang et al. |
| 2005/0267051 | A1 | 12/2005 | Lee et al. |
| 2006/0014738 | A1 | 1/2006 | Wachendorff-neumann et al. |
| 2006/0062742 | A1 | 3/2006 | Davis et al. |
| 2006/0269485 | A1 | 11/2006 | Friedman et al. |
| 2007/0053788 | A1 | 3/2007 | Zhao |
| 2007/0077292 | A1 | 4/2007 | Pinsky |
| 2007/0106393 | A1 | 5/2007 | Miles et al. |
| 2007/0134292 | A1 | 6/2007 | Suokas et al. |
| 2007/0154554 | A1 | 7/2007 | Burgermeister et al. |
| 2007/0170563 | A1 | 7/2007 | Chen |
| 2007/0190066 | A1 | 8/2007 | Savage et al. |
| 2007/0190067 | A1 | 8/2007 | Savage et al. |
| 2007/0190558 | A1 | 8/2007 | Savage et al. |
| 2007/0243225 | A1 | 10/2007 | McKay |
| 2007/0269375 | A1 | 11/2007 | Chen et al. |
| 2008/0085949 | A1 | 4/2008 | McGhee |
| 2008/0124376 | A1 | 5/2008 | Pruitt et al. |
| 2008/0174035 | A1 | 7/2008 | Winterton |
| 2008/0188819 | A1 | 8/2008 | Kloke et al. |
| 2008/0279944 | A1 | 11/2008 | Sawhney |
| 2009/0016973 | A1 | 1/2009 | Ratcliff et al. |
| 2009/0024101 | A1 | 1/2009 | Toshishige et al. |
| 2009/0054295 | A1 | 2/2009 | Vicari et al. |
| 2009/0068122 | A1 | 3/2009 | Pilch et al. |
| 2009/0099531 | A1 | 4/2009 | Griesbach, III |
| 2009/0124591 | A1 | 5/2009 | Diamond et al. |
| 2009/0226884 | A1 | 9/2009 | Tsujimoto et al. |
| 2009/0252781 | A1 | 10/2009 | Sawhney et al. |
| 2009/0279944 | A1 | 11/2009 | Schmitz et al. |
| 2009/0324517 | A1 | 12/2009 | Kline |
| 2010/0022481 | A1 | 1/2010 | Wang et al. |
| 2010/0092398 | A1 | 4/2010 | Reynolds |
| 2010/0209497 | A1 | 8/2010 | Thornthwaite |
| 2010/0226884 | A1 | 9/2010 | Chang et al. |
| 2010/0310478 | A1 | 12/2010 | Fitzgerald et al. |
| 2010/0330086 | A1 | 12/2010 | Savage et al. |
| 2011/0033540 | A1 | 2/2011 | Daniloff et al. |
| 2011/0071099 | A1 | 3/2011 | Bielawska et al. |
| 2011/0091376 | A1 | 4/2011 | Savage |
| 2011/0123624 | A1 | 5/2011 | Zasloff |
| 2011/0135742 | A1 | 6/2011 | Kim et al. |
| 2011/0171144 | A1 | 7/2011 | Wang et al. |
| 2011/0230589 | A1 | 9/2011 | Maggio et al. |
| 2012/0088733 | A1 | 4/2012 | Kim et al. |
| 2012/0107382 | A1 | 5/2012 | Savage |
| 2012/0128793 | A1 | 5/2012 | Miller et al. |
| 2013/0004586 | A1 | 1/2013 | Vachon et al. |
| 2013/0022651 | A1 | 1/2013 | Savage |
| 2013/0034500 | A1 | 2/2013 | Savage et al. |
| 2013/0040265 | A1 | 2/2013 | Park et al. |
| 2013/0053507 | A1 | 2/2013 | Savage |
| 2013/0089580 | A1 | 4/2013 | Boutros |
| 2013/0137668 | A1 | 5/2013 | Fein et al. |
| 2013/0234842 | A1 | 9/2013 | Leitz |
| 2013/0236619 | A1 | 9/2013 | Savage |
| 2013/0243823 | A1 | 9/2013 | Genberg et al. |
| 2013/0243840 | A1 | 9/2013 | Savage et al. |
| 2013/0243842 | A1 | 9/2013 | Genberg et al. |
| 2013/0245760 | A1 | 9/2013 | Savage et al. |
| 2013/0280312 | A1 | 10/2013 | De Szalay |
| 2013/0280391 | A1 | 10/2013 | Savage |
| 2014/0062960 | A1 | 3/2014 | Kim et al. |
| 2014/0107090 | A1 | 4/2014 | Beus et al. |
| 2014/0194401 | A1 | 7/2014 | Genberg et al. |
| 2014/0219914 | A1 | 8/2014 | Govindan et al. |
| 2014/0228905 | A1 | 8/2014 | Bolea |
| 2014/0271761 | A1 | 9/2014 | Savage et al. |
| 2014/0274913 | A1 | 9/2014 | Savage et al. |
| 2014/0305461 | A1 | 10/2014 | Pimenta et al. |
| 2014/0315873 | A1 | 10/2014 | Beus et al. |
| 2014/0336131 | A1 | 11/2014 | Savage et al. |
| 2014/0363780 | A1 | 12/2014 | Vazquez et al. |
| 2014/0369941 | A1 | 12/2014 | Vazquez et al. |
| 2015/0093423 | A1 | 4/2015 | Savage et al. |
| 2015/0110767 | A1 | 4/2015 | Savage et al. |
| 2015/0140063 | A1 | 5/2015 | Savage |
| 2015/0203257 | A1 | 7/2015 | Canegallo |
| 2015/0203527 | A1 | 7/2015 | Savage |
| 2015/0239928 | A1 | 8/2015 | Savage |
| 2015/0258121 | A1 | 9/2015 | Darien et al. |
| 2015/0258122 | A1 | 9/2015 | Beus et al. |
| 2015/0258123 | A1 | 9/2015 | Savage et al. |
| 2015/0314342 | A1 | 11/2015 | Beus et al. |
| 2015/0366880 | A1 | 12/2015 | Genberg et al. |

(56) References Cited

U.S. PATENT DOCUMENTS

| | | | |
|---|---|---|---|
| 2015/0374719 | A1 | 12/2015 | Genberg et al. |
| 2015/0374720 | A1 | 12/2015 | Genberg et al. |
| 2016/0022702 | A1 | 1/2016 | Savage et al. |
| 2016/0045421 | A1 | 2/2016 | Vazquez et al. |
| 2016/0052959 | A1 | 2/2016 | Savage |
| 2016/0096864 | A1 | 4/2016 | Savage |
| 2016/0193232 | A1 | 7/2016 | Beus et al. |
| 2016/0199390 | A1 | 7/2016 | Beus et al. |
| 2016/0311850 | A1 | 10/2016 | Savage et al. |
| 2016/0311851 | A1 | 10/2016 | Savage et al. |
| 2017/0035677 | A1 | 2/2017 | Vazquez et al. |
| 2017/0080128 | A1 | 3/2017 | Genberg et al. |
| 2017/0137459 | A1 | 5/2017 | Savage |
| 2017/0210776 | A1 | 7/2017 | Savage |
| 2017/0232004 | A1 | 8/2017 | Genberg et al. |
| 2017/0258963 | A1 | 9/2017 | Savage et al. |
| 2018/0164221 | A1 | 6/2018 | Singh et al. |
| 2018/0280550 | A1 | 10/2018 | Savage |
| 2019/0076581 | A1 | 3/2019 | Savage et al. |

FOREIGN PATENT DOCUMENTS

| | | | |
|---|---|---|---|
| CA | 2842460 | A1 | 1/2013 |
| CA | 2848567 | A1 | 3/2013 |
| CA | 2888259 | A1 | 4/2014 |
| CA | 2741177 | C | 3/2018 |
| CN | 1236322 | A | 11/1999 |
| CN | 101247838 | A | 8/2008 |
| CN | 101378761 | A | 3/2009 |
| CN | 102145005 | A | 8/2011 |
| CN | 102172356 | A | 9/2011 |
| CN | 104039369 | A | 9/2014 |
| CN | 104080458 | A | 10/2014 |
| CN | 104080459 | A | 10/2014 |
| CN | 107670024 | A | 2/2018 |
| DE | 1037074 | B | 8/1958 |
| EP | 0341951 | A2 | 11/1989 |
| EP | 1208844 | A1 | 5/2002 |
| EP | 1219631 | A1 | 7/2002 |
| EP | 1250849 | A1 | 10/2002 |
| EP | 0832094 | B1 | 2/2004 |
| EP | 1058552 | B1 | 6/2004 |
| EP | 1311531 | B1 | 5/2016 |
| JP | 60-080457 | A | 5/1985 |
| JP | 02-014741 | A | 1/1990 |
| JP | 04-074026 | B2 | 11/1992 |
| JP | 06-153779 | A | 6/1994 |
| JP | 07-501826 | A | 2/1995 |
| JP | 09-248454 | A | 9/1997 |
| JP | 2002-505292 | A | 2/2002 |
| JP | 2002-515019 | A | 5/2002 |
| JP | 2002-255771 | A | 9/2002 |
| JP | 2002-534532 | A | 10/2002 |
| JP | 2002-538093 | A | 11/2002 |
| JP | 2004-506599 | A | 3/2004 |
| JP | 2004-506645 | A | 3/2004 |
| JP | 2009-131625 | A | 6/2009 |
| JP | 2010-059194 | A | 3/2010 |
| JP | 2010-533051 | A | 10/2010 |
| JP | 2010-538074 | A | 12/2010 |
| JP | 2011-527702 | A | 11/2011 |
| JP | 2014-500741 | A | 1/2014 |
| JP | 2014-520900 | A | 8/2014 |
| JP | 2014-530191 | A | 11/2014 |
| JP | 2014-530192 | A | 11/2014 |
| JP | 2017-519036 | A | 7/2017 |
| WO | 93/01829 | A1 | 2/1993 |
| WO | 95/24415 | A1 | 9/1995 |
| WO | 98/05337 | A1 | 2/1998 |
| WO | 98/27106 | A1 | 6/1998 |
| WO | 99/44616 | A1 | 9/1999 |
| WO | 99/45024 | A1 | 9/1999 |
| WO | 00/35375 | A1 | 6/2000 |
| WO | 00/42058 | A1 | 7/2000 |
| WO | 02/14342 | A1 | 2/2002 |
| WO | 02/67979 | A1 | 9/2002 |
| WO | 03/15757 | A1 | 2/2003 |
| WO | 03/66119 | | 8/2003 |
| WO | 03/90799 | A1 | 11/2003 |
| WO | 2004/082588 | A2 | 9/2004 |
| WO | 2004/112852 | A1 | 12/2004 |
| WO | 2007/089903 | A2 | 8/2007 |
| WO | 2007/089906 | A2 | 8/2007 |
| WO | 2007/089907 | A2 | 8/2007 |
| WO | 2007/134176 | A2 | 11/2007 |
| WO | 2008/038965 | A1 | 4/2008 |
| WO | 2008/048340 | A2 | 4/2008 |
| WO | 2008/096149 | A2 | 8/2008 |
| WO | 2009/049370 | A1 | 4/2009 |
| WO | 2009/079066 | A2 | 6/2009 |
| WO | 2009/144708 | A1 | 12/2009 |
| WO | WO 2009/144708 | A | 12/2009 |
| WO | 2010/006192 | A1 | 1/2010 |
| WO | 2010/036427 | A1 | 4/2010 |
| WO | 2010/062562 | A1 | 6/2010 |
| WO | 2011/066260 | A2 | 6/2011 |
| WO | 2011/109704 | A1 | 9/2011 |
| WO | 2012/061651 | A1 | 5/2012 |
| WO | 2013/013221 | A1 | 1/2013 |
| WO | 2013/013223 | A1 | 1/2013 |
| WO | 2013/029055 | A1 | 2/2013 |
| WO | 2013/029059 | A1 | 2/2013 |
| WO | 2013/040265 | A1 | 3/2013 |
| WO | 2013/040269 | A1 | 3/2013 |
| WO | 2013/109236 | A2 | 7/2013 |
| WO | 2013/131060 | A1 | 9/2013 |
| WO | 2013/163359 | A1 | 10/2013 |
| WO | 2013/167743 | A1 | 11/2013 |
| WO | 2014/062960 | A1 | 4/2014 |
| WO | 2014/107740 | A2 | 7/2014 |
| WO | 2014/151411 | A1 | 9/2014 |
| WO | 2015/058087 | A1 | 4/2015 |
| WO | 2015/138716 | A2 | 9/2015 |
| WO | 2015/200815 | A1 | 12/2015 |
| WO | 2016/172543 | A1 | 10/2016 |
| WO | 2016/186821 | A1 | 11/2016 |
| WO | 2017/053355 | A1 | 3/2017 |

OTHER PUBLICATIONS

U.S. Appl. filed Mar. 21, 2016, Beus et al., U.S. Appl. No. 15/076,313.
U.S. Appl. filed Mar. 23, 2018, Savage, Paul B., U.S. Appl. No. 15/934,534.
U.S. Appl. filed Mar. 9, 2017, Savage et al., U.S. Appl. No. 15/454,135.
U.S. Appl. filed May 3, 2017, Savage et al., U.S. Appl. No. 15/585,632.
U.S. Appl. filed Oct. 16, 2014, Savage, et al., U.S. Appl. No. 14/515,858.
U.S. Appl. filed Oct. 30, 2014, Savage, et al., U.S. Appl. No. 14/398,094.
U.S. Appl. filed Oct. 6, 2015, Savage., U.S. Appl. No. 14/875,953.
U.S. Appl. filed Sep. 1, 2015, Genberg et al., U.S. Appl. No. 14/842,582.
U.S. Appl. filed Sep. 20, 2016, Genberg et al., U.S. Appl. No. 15/270,876.
U.S. Appl. filed Sep. 25, 2015, Savage., U.S. Appl. No. 14/866,213.
U.S. Appl. filed Sep. 9, 2015, Genberg et al., U.S. Appl. No. 14/848,819.
U.S. Appl. No. 14/288, 126, filed May 27, 2014, Savage et al.
U.S. Appl. No. 14/926,738, filed Oct. 29, 2015, Vazquez et al.
U.S. Appl. No. 16/184,211, filed Nov. 8, 2018, Savage.
U.S. Application filed Feb. 17, 2015, by Savage, U.S. Appl. No. 14/624,200.
U.S. Application filed Mar. 10, 2015, by Darien et al., U.S. Appl. No. 14/642,905.
U.S. Application filed Apr. 22, 2016 by Savage et al., U.S. Appl. No. 15/135,900.
U.S. Application filed Apr. 22, 2016 by Savage et al., U.S. Appl. No. 15/135,928.

(56) References Cited

OTHER PUBLICATIONS

U.S. Application filed Apr. 22, 2016 by Savage et al., U.S. Appl. No. 15/135,969.
U.S. Application filed Jul. 29, 2014, by Vazquez et al., U.S. Appl. No. 14/364,283.
U.S. Application filed Oct. 1, 2015, by Savage et al., U.S. Appl. No. 14/873,013.
U.S. Application filed Oct. 25, 2016, by Vazquez et al., U.S. Appl. No. 15/333,514.
U.S. Patent Application filed Apr. 23, 2015 by Beus et al., U.S. Appl. No. 14/694,028.
U.S. Patent Application filed Aug. 19, 2015,by Savage, U.S. Appl. No. 14/830,356.
U.S. Patent Application filed Feb. 13, 2018, by Genberg, et al., U.S. Appl. No. 15/895,848.
U.S. Patent Application filed Jul. 23, 2014 2014 by Vazquez et al., U.S. Appl. No. 14/339,342.
U.S. Patent Application filed Jul. 25, 2014, by Savage et al., U.S. Appl. No. 14/341,304.
Uncategorized: CSA Biotechnologies LLC, Apr. 5, 2011.
US. Appl. filed Mar. 1, 2013, Savage., U.S. Appl. No. 13/783,007.
Valkonen, et al., "Bile acid amidoalcohols: simple orqanoqelators", Biosens Bioelectron, Dec. 2004.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008, pp. 124-134.
Van Den Bogaard et al., "Antibiotic Usage in Animals: Impact on Bacterial Resistance and Public Health"; 1999; Drugs; 58 (4): 589-607.
Weijian YE et al "Synthesis and antibacterial activity of new long-chain-alkyl bile acid-based amphiphiles", Bioorganic Chemistry, vol. 51, Aug. 19, 2013, pp. 1-7, XP55513451, US ISSN: 0045-2068, DOI:10.1013/i.bioorg.2013.08.003.
Weijian YE et al "Synthesis and antibacterial activity of new long-chain-alkyl bile acid-based amphiphiles", Bioorganic Chemistry, vol. 51, Aug. 19, 2013, pp. 1-7, XP55513451, US ISSN: 0045-2068, DOI:10.1013/i.bioorq.2013.08.003.
Welling et al., "Radiochemical and biological characteristics of99m-Tc-UBI 29-41 for imaging of bacterial infections", Nuclear Medicine and Biology 29 (2002) 413-422.
Willemen et al., "Miceli Formation and Antimicrobial Acivity of Cholic Acid Derivatives with three Permanent Ionic Head Groups", Angew. Chem. Int. Ed., 2002, 41, No. 22.
Williams et al., "In vivo efficacy of a silicone-cationic steroid antimicrobial coating to prevent implant-related infection", Biomaterials, Nov. 2012: 33(33): 8641-8656 (Department of Brigham Young University).
Winter et al., "Improved paragmentic chelate for molecular imaging with MRI", 2005 J. Magn. Magn. Mater. 293: 540-545.
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
Xin-Zhong Lai, et al.,"Ceragenins: Cholic Acid-Based Mimics of Antimicrobial peptides", Account of Chemical Research vol. 41, No. 10, Oct. 21, 2008, pp. 1233-1240.
Zanger et al., "Structure-Activity Relationship and Drug Design", Remington's Pharmaceutical Sciences, Chapter 27, 16th Edition, 1980, pp. 420-425.
Zaragoza Dorwald, Side Reactions in Organic Synthesis, 2005, Wiley-VCH Verlag GmbH & Co. KGaA, Weinheim, Preface. p. IX.
Graterol et al., "Ultrastructural changes in premalignant and malignant lesions of the uterine cervix with papillomavirus infection", Journal of Cancer Research and Experimental Oncology, vol. 2, No. 3, Sep. 2010, pp. 35-42.
Guan et al.; "Preparation and Characterization of Cholic Acid-Derived Antimicrobial Agents with Controlled Stabilities"; 2000; Organic Letters; 2(18): 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/010062704/suppl file/o10062704 sl.pdf.
Hao et al., "A Phase I and Pharmacokinetic Study of Squalamine, an Aminosterol Angiogenesis Inhibitor", Clin Cancer Res, vol. 9, 2003, pp. 2465-2471.
Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
Interational Search Report for PCT Application No. PCT/US2009/0475485 dated Feb. 17, 2010.
International Preliminary Report on Patentability received for PCT Patent Application No. PCT/US20/034297, mailed on Dec. 2, 2021, 6 pages.
International Search Report and Written Opinion received for PCT Patent Application No. PCT/US2020/034297, mailed on Aug. 26, 2020, 8 pages.
International Search Report for PCT Aoolication No. PCT/US2011/059225 dated Jan. 31, 2012.
International Search Report for PCT Application No. PCT/US2012/047750, dated Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2013/065510, dated Apr. 30, 2015.
International Search Report for PCT Application No. PCT/US2014/034986 dated Aug. 28, 2014.
International Search Report for PCT Application No. PCT/US2015/020166 dated Sep. 2, 2015.
International Search Report for PCT Application No. PCT/US2015/038029 dated Sep. 29, 2015.
International Search Report for PCT Application No. PCT/US2018/023566 dated Mar. 21, 2018.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Jacob; Feeding Fishmeal to Poultry; https://articles.extension.org/pages/67357/feeding-fishmeal-to-poultry; May 5, 2015; accessed Sep. 10, 2018 (Year: 2015).
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824, 2002.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Kaltsas et al., Endocrine-Related Cancer (2005) 12 683-699.

(56) References Cited

OTHER PUBLICATIONS

Kuroda, et al., "Ceragenin CSA-13 induces cell cycle arrest and antipro liferative effects in wild-type and p52 null mutant HCT116 colon cancer cells", Preclinical Report, Wolters Kluwer Health 2013.

Kwon, Ed., Polymeric Drug Delivery Systems, Taylor & Francis Group, LLC; pp. 1-653, 2005, pp. 350-351.

Lai XZ ( Ceragenins: cholic acid-based mimics of antimicrobial peptides. Acc Chern Res. Oct. 2008;41 (10): 1233-40. doi: 10.1021/ar700270t. Epub Jul. 11, 2008. PMID: 18616297.

Lai, et al., "Controlled Released of a Bactericidal Ceragenin-Polymer Conjugate", Sep. 227, 2006, oa. 1, 46th Annual Interscience Conference on Antimicrobial Agents and Chemotherapy.

Lankinen et al., "Ga-Data-Peptide Targeting VAP-1 for In Vivo Evaluation of Inflammatory and Infectious Bone Conditions", 52nd Annual Meeting of the Orthopaedic Research Society.

Lawrence, Toby (The Nuclear Factor NF-?B Pathway in Inflammation, Cold Spring Harb Perspect Biol. Dec. 2009;1(6): a001651).

Leszczynska et al. (J Antimicrob Chemother, published Nov. 7, 2012), Bacterial activity of cationic lipids, pp. 1-9).

Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.

Li et al., "Incremental conversin of Outer-Membrane Permeabilizers into Potent Antibiotics for Gram-Negative Bacteria", J. Am. Chem. Soc. 1999, 121, 9310-940.

Li, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.

Louw et al., "Recueil des Travaux Chimiques des Pays-Bas et la Belgique", vol. 73, pp. 667-676, 1954.

Lowe et al., "Effect of Hydrophobicity of a Drug on its Release from Hydrogels with Different Topological Structures" Journal of Polymer Science (1999) 73: 1031-1039 (9 pages).

Martin, L., WebMD, 2012, pp. 1-25.

Martindale: the complete drug reference, Cetrimide; Cetylpyridinium chloride Ed-Parfitt K, Jan. 1, 2000, pp. 1105-1106.

Massoud et al., "Molecular imaging in living subjects: seeing fundamental biological processes in a new light", Genes & Development 17: 545-580 2003, Cold Spring Harbor Laboratory Press.

McIntosh et al., "Towards Non-Invasive Screening of Skin Lesions by Near-Infrared Spectroscopy", The Journal of Investigative Dermatology, vol. 116, No. 1, 2001, pp. 175-181.

Melinda Yin, et al., "Antiangiogenic Treatment Delays Chondrocyte Maturation and Cone Formation During Lim Skeletogenesis", Journal of Vone and Mineral Research, American Society for Bone and Mineral Research, New York, NY, US, vol. 17, No. 1, Jan. 1, 2002.

Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.

Munoz-Juarez et al., "Wide-Lumen Stapled Anastomosis vs. Conventional End-to-End Anastomosis in the Treatment of Crohn's Disease", Dis Colon Rectum 2001; 44: No. 1, 20-26.

No author listed. Novel antibiotic coating shows potential for use on surgical implants. Healio website. Dec. 21, 2005. healio.com/orthopedics/news/online/%7BdcOe6031-1f10-4b3c-abf6-f50b9cfd683f%7D/novel-antibiotic-coating-shows-potential-for-use-on-surgical-implants. Accessed Jun. 2, 2019. (Year: 2005).

Novy et al., "Infections as a Cuase of Infertility", Glob. Libr. Women's med., (ISSN: 1756-2228) 2008; DOI 10.3843/GLOWM.10328.

Ogata et al. Intramammary application of ozone therapy to acute clinical mastitis in dairy cows. J. Vet. Med. Sci. 62(7):681-686, 2000.

Shi et al., CN 107670024 A, English translation, publ. Feb. 9, 2018 (Year: 2018).

"Mouth rinse" definition by Medical dictionay. Retrieved from http://medical-dictionary.thefreedictionary.com/mouth-i-rinse.

"Quaternary Ammoniuim Compounds", Van Nostrand's Scientific Encyclopedia, Jan. 1, 2006, John Wiley & Sons, Inc.

"Structure-Activity Relationship and Drug Design." Remington's Pharmaceutical Sciences. Sixteenth Edition. Mack Publishing, 1980, pp. 420-425.

Ahmed, Hydrogel: Preparation, characterization, and applications: A review, Journal of Advanced Research (2015) 6: 105-121 (Year: 2015).

Alafort et al., "Lys and Arg in UBI: A specific site for a stable Tc-99m complex?", Nuclear Medicine and Bioloav 30 (2003) 605-615.

Alhanout K et al: "Squalamine as an example of a new potent antimicrobial agents class: a critical review.", Current Medicinal Chemistry 2010, vol. 17, No. 32, 2010, pp. 3909-3917.

Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN 0040-4039, DOI: 10. 1016/S0040-4039(99)00075-1.

Bakri et al., "Inhibitory effect of garlic extract on oral bacteria", Archives of Oral Biology, 50: 645-651.

Barton, Journal of Clinical Investigation, vol. 118, No. 2, Feb. 2008, Review Series, pp. 413-420.

BASF, [Retrieved from internet <URL:https://wor1daccount.basf.com/wa/NAFTA.about.en_US/Catalog/ChemicalsNAFTA-/doc4/BASF/PRD/30085231/.pdf?asset type=pi/pdf&language=EN&um=um:documen-tum: mCommerce solEUi09007bb280022b53.pdf >1 (Year: 2004).

BASF, Pluronic (Registered) Block Copolymer NF Grades (Poloxamer NF Grades), Technical Bulletive (2004).

Belikov V.G., Pharameutical Chemistry, M., Higher School, 1993, p. 43-47.

Bellini et al., "Cholic and deoxycholic acids derivatives (Part I). Antimicrobial activity of cholane compounds", European J. of Medicinal Chem., 18(2), pp. 185-190, 1983.

Bellini et al., "Cholic and deoxycholic acids derivatives (Part II). Antimicrobial activity of cholane compounds", European J. of Medicinal Chem., 18(2), pp. 191-195, 1983.

Berge et al., Pharmaceutical salts. Journal of Pharmaceutical Sciences, vol. 66(1), pp. 1-19 (Year: 1977).

Bondaryk, M. et al., "Antifungal agents commonly used in the superficial and mucosal candidiasis treatment: mode of action and resistance development", Postep. Derm., Alergol., vol. 30, No. 5, pp. 293-301.

Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.

Britton et al, "Imaging bacterial infection with 99mTc-ciprofloxacin (Infection)", Journal of Clinical Pathology, vol. 55, pp. 817-823, Apr. 6, 2015.

Brown, "Bioisosteres in Medicinal Chemistry, First Edition", edited by Nathan Brown, 2012, Ch. 2 Classical Bioisosteres, pp. 1-52.

Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.

Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.

Bush, "Staphylococcal Infections", Merck Manuals Professional Edition, http://www.merckmanuals.com/professional/infectious-diseases/gram-positiv- e-cocci/staphylococcal-infections, 2017.

Chen et al, J Drug Target, Dec. 2012; 20(10):856-63, 892.

Chin et al, "Antimicrobial Activities of Ceragenins against Clinical Isolates of Resistant *Staphylococcus aureas*", Antimicrobial Agents and Chemotherapy, vol. 51, No. 4, Apr. 2007, p. 1268-1273.

Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.

Cipolla et al., "Inhaled antibiotics to treat lung infection", Pharm Pat Anal., Sep. 2013.

(56) References Cited

OTHER PUBLICATIONS

Clara et al., "Preclinical evaluation of magainin-A as a contraceptive antimicrobial agent", Fertility and Sterility 81 (5), pp. 1357-1365, 2004.
csabiotech.com, Uncategorized: CSA Biotechnologies LLC. posted by admin on Apr. 5, 2011 (Year: 2011).
Czernomysy-Furowicz et al. Etiological agents of mastitis in dairy cows on a farm in the West Pomeranian Region. Acta Sci. Pol., Zootechnica 7(1) 2008, 3-10.
De Cuyper et al., "Surface functionalization of magnetoliposomes in view of improving iron oxide-based magnetic resonance imaging contrast agents: Anchoring of gadolinium ions to a lipophilic chelate", 2007 Anal. Biochem. 367: 266-273. Published online May 10, 2007.
De Haas et al. Associations between pathogen-specific cases of clinical mastitis and somatic cell count patterns. J. Dairy Sci. 87: 95-105.
Dean et al.; Flavor Associated with Fish Meal in Diets Fed to Broiler Chickens; 1968; Can. J. Animal Sci.; 49:11-15 (Year: 1968).
Deepak B. Salunke et al., "Amino Functionalized Novel Cholic Acid Derivatives Induce HIV-1 Replication and Syncytia Formation in T Cells", J. Med. Chem. 2006.
Dennison et al., "Anticancer a-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Ding, et al., "Correlation of the Antibacerial Activities of Cationic Peptid Antibiotics and Cationic Steroid Antibiotics", J. Med. Chem., vo. 45, pp. 663-669 (Year: 2002).
Ding, et al., "Origins of cell selectivity of cationic steroid antibiotics", Journal of American Chemical Society, Oct. 2004, pp. 13642-13648.
Dorwald, "Side reactions in organic synthesis", 2005, Wiley-VCH Verlag GmbH & co., KGAA Weinhelm, Preface. p. IX.
Dumortier G, (A review of poloxamer 407 pharmaceutical and pharmacological characteristics. Pharm Res. Dec. 2006;23(12):2709-28. doi: 10.1007/S11095-006-9104-4. Epub Nov. 11, 2006. PMID: 17096184.).
Dumortier, Getal. (Pharmaceutical Research, vol. 23, No. 12, Dec. 2006).
Elder et al., "The Utility of Sulfonate Salts in Drug Development", Journal of Pharmaceutical Sciences 99(7): 2948-2961, 2010.
Emily L. Perry et al., "Assessing peri-implant tissue infection prevention in a percutaneous model", Journal of Biomedical Materials Research Part B: Applied Biomaterials, vol. 028, Nov. 19, 2009, pp. 397-408.
Epand et al., "Bacterial lipid composition and the antimicrobial efficacy of cationic steroid compounds (Ceragenins)", BBA, 2007, pp. 65-78.
Erskine et al., "Mastitis in Cattle", Merck Manual: Veterinary Manual. Electronic Resource: [http://www.merckvetmanual.com/reproductive-system/mastitis-in-large-animals/mastitis-in-cattle], retrieved Mar. 8, 2017.
European Search Report received for EP Patent Application No. 20810836.5, mailed on Jun. 30, 2022, 7 pages.
Examiner Interview Summary received for U.S. Appl. No. 14/208,082, mailed on Oct. 23, 2020, 4 pages.
Feng, Theses Brigham Young University, BYU Scholars Archive, dated Dec. 19, 2011, 892.
Fichna et al., "Synthesis of Target-Specific Radiolabeled Peptides for Diagnostic Imaging", Bioconjugate Chem., 2003, 14, 3-17, American Chemical Society.
Food definition, Merriam Webster, https://www.merriam-webster.com/ dictionary/food, Accessed Feb. 12, 2018.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
Opsenica D, et al., "Cholic Acid Derivatives as 1,2,4,5-Tetraoxane Carriers: Structure and Antimalarial and Antiproliferative Activity", J. Med Chem. Aug. 2000.
Oxford Dictionaries (on-line) definition of Adsorb ([Retrieved from internet <URL: http://www.oxforddictionaries.com/us/definition/american_english/adsorb >] [Downloaded Mar. 10, 2015]).
P B Savage et al: "Thin Films Containing Ceragenins Prevent Biofilm Formation on Endotracheal Tubes", 9th International Federation of Infection Control Congress, Oct. 14, 2008 (Oct. 14, 2008), pp. 1-1, XP55016800, Santiago, Chile Retrieved from the Internet: URL:http://www.n8medical.com/PDF/EndotrachealTubePoster-IFIC.PDF[retrieve- d on Jan. 18, 2012].
P. B. Savage, et al., "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Papo et al., "Host defense peptides as new weapons in cancer treatment", Cmls Cellular And Molecular Life Sciences, vol. 62, No. 7-8, Apr. 1, 2005, pp. 784-790.
Papo et al., "Host peptides as new weapons in cancer treatment", CMLS Cell. Mol. Life Sci. 62 (2005), 784-790.
Paul B. Savage, et al: "Antibacterial Properties of cationic steroid antibiotics", FEMS Microbiology Letters, vol. 217, Nov. 2002, pp. 1-7.
Perry et al., "Assessing peri-implant tissue infection prevention in a percutaneous model", Journal of Biomedical Materials Research Part B: Applied Biomaterials, vol. 028, Nov. 19, 2009, pp. 397-408.
Piktel et al. Sporicidal Activity of Ceragenin CSA-13 Against Bacillus Subtillis, Scientific Reports, vol. 7, Mar. 15, 2017 [retrieved on Apr. 24, 2018. Retreived from the internet: <URL: https://www.nature.com/articles/srep44452.pdf> Entire Document.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.
Pollard et al. (J Antimicrob Chemother 2012; 67:2665-2672).
Press release (Ceragenix Pharmaceuticals, Wayne State University, Brigham Young University, Systemic Anti-Infectives, Pre-clinical Title-Ceragenin (Trademark) Compound demonstrates potent activity against multidrug resistant bacterial strains of Pseudomonas, Denver, CO—Published Dec. 20, 2007).
Pycock, "The Dirty Mare", https://www.equine-reproduction.com/articles/DirtyMare.shtml, 2003.
Rausch, Virtual Textbook of Organic Chemistry, Heterocyclic Chemistry, 1999, pp. 1-14, recovered from https://www2.chemistry.msu.edu/faculty/reusch /VirtTxtJml/heterocy.htm on Jun. 1, 2017.
Robert Bucki (Resistance of the antibacterial agent ceragenin CSA-13 to inactivation by DNA or F-actin and its activity in cystic fibrosis sputum, Journal of Antimicrobial Chemotherapy, vol. 60, Issue 3, Sep. 2007, pp. 535-545).
Roohi et al., Prepration, quality control and biological evaluation of 99m-Tc-labelled cationic steroid antibiotic (CSA-13), Radiochim. Acta 197, 57-62 (2009).
Savage, et al., "Antibacterial Activities of Thin Films Containing Ceragenins", Microbial Surfaces: Structure, Interactions and Reactivity, ACS, May 30, 2008, pp. 65-78.
Schiller et al., "Potentiation of Platinum Antitumor Effects in Human Lung Tumor Xenografts by the Angiogenesis Inhibitor Squalamine: Effects on Tumor Neovascularization", Clin Cancer Res., vol. 5, 1999, pp. 4287-4294.
Schmidmaier et al., "Local Application of Growth Factors (Insulin-Like Growth Factor-1 and Transforming Growth Factor-(Beta) 1)

(56) References Cited

OTHER PUBLICATIONS

From a Biodegradable Poly(D, L-lactide) Coating of Osteosynthetic Implants Accelerates Fracture Healing in Rats", Bone vol. 28 No. 4, Apr. 2001.
Sentamilselvi et. al., International Journal of Trichology, vol. 1, Issue 2, pp. 100-108, Jul. 2009.
Shi et al., "Multi-center randomized double-blind clinicial trail on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sigma-Aldrich, Poly(ethylene-co-vinyl acetate), [Retrieved from internet <URL: http://www.sigmaaldrich.com/catalog/product/aldrich/340502?lang=-en®ion=US >], [Downloaded Jul. 22, 2016], excerpt in action.
Sigma-Aldrich, Poly(ethylene-co-vinyl acetate), [Retrieved from internet <URL:http://www.sigmaaldrich.com/catalog/product/aldrich/3405027lang—en (Registered) ion=US >], [Downloaded Jul. 22, 2016], excerpt in action.
Sinclair et al., "Development of a broad spectrum polymer-released antimicrobial coating for the prevention of resistant strain bacterial infections", Journal of Biomedical Materials Research Part A, vol. 1DOA, No. 10, May 24, 2012, pp. 2732-2738.
Staphylococcal Infections (Electronic Resource; Merck Manual). Retrieved on Jul. 3, 2017: [http://www.merckmanuals.com/professional/infectious-diseases/gram-positive-cocci/staphylococcal-infections].
Steeneveld et al. Cow-specific treatment of clinical mastitis: an economic approach. J. Diary. Sci. 94: 174-188, 2011.
Survey Research on Behcet's Disease, 2005 to 2007 Comprehensive Survey Reports, 2008, pp. 34-39.
Suzuki et al.; "Molecular Genetics of Plant Sterol Backbone Synthesis"; 2007; Lipids; 42: 47-54.
U.S. Appl. filed Apr. 22, 2016, Savage et al., U.S. Appl. No. 15/135,900.
U.S. Appl. filed Apr. 22, 2016, Savage et al., U.S. Appl. No. 15/135,928.
U.S. Appl. filed Apr. 22, 2016, Savage et al., U.S. Appl. No. 15/135,969.
U.S. Appl. filed Apr. 23, 2015, Beus et al., U.S. Appl. No. 14/694,028.
U.S. Appl. filed Apr. 7, 2017, Savage., U.S. Appl. No. 15/481,184.
U.S. Appl. filed Apr. 7, 2017, Savage., U.S. Appl. No. 15/481,884.
U.S. Appl. filed Aug. 19, 2015, Savage., U.S. Appl. No. 14/830,356.
U.S. Appl. filed Feb. 13, 2018, Genberg, et al., U.S. Appl. No. 15/895,848.
U.S. Appl. filed Feb. 17, 2015, Savage., U.S. Appl. No. 14/624,200.
U.S. Appl. filed Jan. 16, 2017, Savage., U.S. Appl. No. 15/406,667.
U.S. Appl. filed Jan. 21, 2015, Savage., U.S. Appl. No. 14/602,071.
U.S. Appl. filed Jan. 22, 2015, Savage., U.S. Appl. No. 14/602,499.
U.S. Appl. filed Jul. 23, 2014, Vazquez et al., U.S. Appl. No. 14/339,342.
U.S. Appl. filed Jul. 25, 2014, Savage, et al., U.S. Appl. No. 14/341,304.
U.S. Appl. filed Jun. 25, 2015, Genberg et al., U.S. Appl. No. 14/750,928.
U.S. Appl. filed Mar. 1, 2013, Savage, Paul B., U.S. Appl. No. 13/783,007.
U.S. Appl. filed Mar. 11, 2015, Beus et al., U.S. Appl. No. 14/644,946.
U.S. Appl. filed Mar. 11, 2015, Savage et al., U.S. Appl. No. 14/645,040.
U.S. Appl. filed Mar. 20, 2018, Savage et al., U.S. Appl. No. 15/926,577.

* cited by examiner

LL-37

CSA-13

METHODS FOR TREATING LUNG INFECTIONS AND INFLAMMATION

CROSS-REFERENCE TO RELATED APPLICATION

This application is a continuation of U.S. application Ser. No. 14/515,858, filed Oct. 16, 2014, which claims the benefit of U.S. Provisional App. No. 61/892,263, filed Oct. 17, 2013, which are incorporated herein in their entirety.

BACKGROUND OF THE INVENTION

1. The Field of the Invention

Cationic steroidal antimicrobials ("CSAs" or ceragenins) and formulations thereof for treating certain diseases and symptoms such as lung infections and lung inflammation.

2. Description of the Related Art

Cystic fibrosis (CF), or mucoviscidosis, is an autosomal recessive genetic disorder that critically affects the lungs, the pancreas, the liver, and the intestine. A hallmark sign of CF is abnormal transport of chloride and sodium across an epithelium, which leads thick, viscous secretions. CF is caused by a mutation in the gene for the cystic fibrosis transmembrane conductance regulator (CFTR) protein. CFTR regulates the movement of chloride and sodium ions across epithelial membranes, such as the alveolar epithelia located in the lungs. Difficulty breathing is the most serious symptom of CF. This results from clogging of the airways due to mucus build-up, decreased mucociliary clearance, and resulting inflammation. Inflammation and infection cause injury and structural changes to the lungs, leading to a variety of symptoms. Many of these symptoms occur when bacteria that normally inhabit the thick mucus grow out of control and cause pneumonia. In advanced CF, changes in the architecture of the lung further exacerbate difficulties in breathing. Other symptoms of CF include coughing up blood (hemoptysis), high blood pressure in the lung (pulmonary hypertension), heart failure, difficulties getting enough oxygen to the body (hypoxia), and respiratory failure requiring support with breathing masks, such as bilevel positive airway pressure machines or ventilators. *Staphylococcus aureus, Haemophilus influenzae*, and *Pseudomonas aeruginosa* are the three most common organisms causing lung infections in CF patients.

Chronic obstructive pulmonary disease (COPD), also known as chronic obstructive lung disease (COLD), chronic obstructive airway disease (COAD), chronic airflow limitation (CAL), and chronic obstructive respiratory disease (CORD), is a lung disease defined by persistently poor airflow as a result of breakdown of lung tissue (known as emphysema) and dysfunction of the small airways. The most common symptoms of COPD are sputum production, shortness of breath, and a productive cough.

Inflammation is implicated in the development of COPD. Inflammation is a biological response to harmful stimuli, such as pathogens, damaged cells, or irritants. As such, inflammation is a major component of the nonspecific defense system. The classical signs of acute inflammation are pain (dolor), heat (calor), redness (rubor), swelling (tumor), and loss of function. Although infection is caused by a microorganism, inflammation is one of the responses by the infected subject to the pathogen.

Endogenous antimicrobial peptides, such as the human cathelicidin LL-37, play key roles in innate immunity against pathogens. LL-37 is found in airway mucus of the lungs and is believed to be important in controlling bacterial growth in the lung. Antimicrobial peptides are found in a wide variety of organisms such as mammals, amphibians, insects, and plants. Thus, antimicrobial peptides appear to be one of "Nature's" primary means of controlling bacterial growth. Indeed, there are thousands of examples of antimicrobial peptides known in the art. The primary sequences of these peptides vary substantially, but the adopted morphologies sometimes have similarities. Thus, one can make some broad generalizations regarding their structure. Those that adopt alpha helix conformations juxtapose hydrophobic side chains on one face of the helix with cationic (positively charged) side chains on the opposite side. A similar morphology is found in antimicrobial peptides that form beta sheet structures: hydrophobic side chains on one face of the sheet and cationic side chains on the other.

Clinical use of antimicrobial peptides presents significant issues including the relatively high cost of producing peptide-based therapeutics, the susceptibility of peptides to proteases generated by the host and by bacterial pathogens, and deactivation of antimicrobial peptides by proteins and DNA in lung mucosa. Indeed, high salt, protein and DNA concentration in CF sputa combine to significantly deactivate endogenous antimicrobial peptides and play a role in rendering CF patients vulnerable to recurrent infections.

BRIEF SUMMARY OF THE INVENTION

Cationic steroidal antimicrobials ("CSAs" or "ceragenins") represent a new class of small molecule, non-peptide mimics of antimicrobial peptides. These compounds approximate the amphiphilic morphology in antimicrobial peptides and display potent, broad-spectrum antibacterial activity. (See, e.g., FIG. 1). Such compounds also display the ability to modulate inflammatory responses. See, e.g. U.S. Patent Publication No. US 2014/0274913 and U.S. Pat. No. 11,524,015. Accordingly, CSAs represent a viable new drug class for treating various infections, affording surprising anti-pathogenic and anti-inflammatory activities.

Some embodiments are directed to a method of treating a lung infection with a cationic steroidal antimicrobial (CSA), comprising: administering to a lung via inhalation into the lung a therapeutically effective amount of an anti-pathogenic substance comprising at least one cationic steroid antimicrobial (CSA), or a pharmaceutically acceptable salt thereof, to a patient in need of treatment, wherein the CSA administration treats the lung infection.

In some embodiments, the lung infection is a bacterial lung infection.

In some embodiments, the lung infection is drug-resistant.

In some embodiments, the lung infection is antibiotic-resistant.

In some embodiments, the lung infection is tobramycin-resistant, vancomycin-resistant, or methicillin-resistant.

In some embodiments, the lung infection is a chronic lung infection.

In some embodiments, the lung infection is an infection by *Staphylococcus, Haemophilus, Pseudomonas, Burkholderia, Aspergillus, Scedosporium, Candida, Exophiala, Penicillium*, or *Acrophialophora* pathogens.

In some embodiments, the lung infection is an infection by *Staphylococcus aureus, Haemophilus influenzae, Pseudomonas aeruginosa, Burkholderia cepacia, Aspergillus fumigatus, Aspergillus flavus, Aspergillus nidulans,*

*Aspergillus terreus, Scedosporium apiospermum, Scedosporium prolificans, Candida albicans, Exophiala dermatitidis, Penicillium emersonii*, or *Acrophialophora fusispora* pathogens.

In some embodiments, the patient has cystic fibrosis.

In some embodiments, the patient has allergic bronchopulmonary aspergillosis.

In some embodiments, the lung infection has resulted in the formation of a biofilm.

Some embodiments comprise administering an effective amount of at least two different anti-pathogenic substances.

Some embodiments comprise administering an effective amount of one or more CSAs via inhalation into the lung(s), such as in aerosol or particulate form, to a patient in need thereof.

Some embodiments comprise administering an effective amount of at least two different anti-pathogenic substances, wherein the administration is concurrent.

Some embodiments comprise administering an effective amount of at least two different anti-pathogenic substances, wherein the administration is sequential.

Some embodiments comprise administering an effective amount of at least two different anti-pathogenic substances, wherein both anti-pathogenic substances are CSAs and both are administered via inhalation into the lung(s).

Some embodiments comprise administering an effective amount of at least two different anti-pathogenic substances, wherein the first anti-pathogenic substance is a CSA and the second anti-pathogenic substance is a non-CSA antibiotic.

Some embodiments comprise administering an effective amount of at least two different anti-pathogenic substances, wherein the first anti-pathogenic substance is a CSA and the second anti-pathogenic substance is an antibiotic selected from the group consisting of an aminoglycoside, an ansamycin, a carbacephem, a carbapenem, a cephalosporin, a glycopeptide, a lincosamide, a lipopeptide, a macrolide, a monbactam, a nitrofuran, an oxazolidonone, a penicillin, a polypeptide, a quinolone, a sulfonamide, and a tetracycline.

Some embodiments comprise administering an effective amount of at least two different anti-pathogenic substances, wherein the first anti-pathogenic substance is a CSA and the second anti-pathogenic substance is tobramycin, colistin, aztreonam, ciprofloxacin, azithromycin, erythromycin, or vancomycin.

Some embodiments comprise administering an effective amount of at least two different anti-pathogenic substances, wherein the first anti-pathogenic substance is a CSA and the second anti-pathogenic substance is an antifungal.

Some embodiments further comprise administering an expectorant.

Some embodiments further comprise administering a medication that loosens secretions.

Some embodiments further comprise administering a medication that loosens secretions, wherein the medication that loosens secretions is dornase alfa or hypotonic saline and the secretion is mucus or sputum.

Some embodiments further comprise administering a medication that loosens secretions, wherein the medication that loosens secretions is a deoxyribonuclease enzyme or saline and the secretion is mucus or sputum.

In some embodiments, the CSA further reduces lung inflammation.

In some embodiments, the CSA further reduces lung inflammation mediated by a tumor necrosis factor.

Some embodiments are directed to a method of reducing lung inflammation with a cationic steroidal antimicrobial (CSA), comprising: administering to the lung via inhalation into the lung a therapeutically effective amount of a therapeutic substance comprising at least one cationic steroid antimicrobial (CSA), or a pharmaceutically acceptable salt thereof, to a patient in need of treatment, wherein the CSA administration reduces lung inflammation.

In some embodiments, the lung inflammation results from a bacterial lung infection.

In some embodiments, the lung inflammation results from a bacterial lung infection that is drug-resistant.

In some embodiments, the lung inflammation results from a bacterial lung infection that is antibiotic-resistant.

In some embodiments, the lung inflammation results from a bacterial lung infection that is tobramycin-resistant, vancomycin-resistant, or methicillin-resistant.

In some embodiments, the lung inflammation results from a chronic lung infection.

In some embodiments, the lung inflammation results from an infection by *Staphylococcus, Haemophilus, Pseudomonas, Burkholderia, Aspergillus, Scedosporium, Candida, Exophiala, Penicillium*, or *Acrophialophora* pathogens.

In some embodiments, the lung inflammation results from an infection by *Staphylococcus aureus, Haemophilus influenzae, Pseudomonas aeruginosa, Burkholderia cepacia, Aspergillus fumigatus, Aspergillus flavus, Aspergillus nidulans, Aspergillus terreus, Scedosporium apiospermum, Scedosporium prohficans, Candida albicans, Exophiala dermatitidis, Penicillium emersonii*, or *Acrophialophora fusispora* pathogens.

In some embodiments, the patient has cystic fibrosis.

In some embodiments, the patient has allergic bronchopulmonary aspergillosis.

In some embodiments, the patient has chronic obstructive pulmonary disease.

Some embodiments comprise administering an effective amount of at least two different therapeutic substances.

Some embodiments comprise administering an effective amount of at least two different therapeutic substances, wherein the administration is concurrent.

Some embodiments comprise administering an effective amount of at least two different therapeutic substances, wherein the administration is sequential.

Some embodiments comprise administering an effective amount of at least two different therapeutic substances, wherein both therapeutic substances are CSAs and both are administered via inhalation into the lung(s).

Some embodiments comprise administering an effective amount of at least two different therapeutic substances, wherein the first therapeutic substance is a CSA and the second therapeutic substance is a Non-CSA antibiotic.

Some embodiments comprise administering an effective amount of at least two different therapeutic substances, wherein the first therapeutic substance is a CSA and the second therapeutic substance is an antibiotic selected from the group consisting of an aminoglycoside, an ansamycin, a carbacephem, a carbapenem, a cephalosporin, a glycopeptide, a lincosamide, a lipopeptide, a macrolide, a monbactam, a nitrofuran, an oxazolidonone, a penicillin, a polypeptide, a quinolone, a sulfonamide, and a tetracycline.

Some embodiments comprise administering an effective amount of at least two different therapeutic substances, wherein the first therapeutic substance is a CSA and the second therapeutic substance is tobramycin, colistin, aztreonam, ciprofloxacin, azithromycin, erythromycin, or vancomycin.

Some embodiments comprise administering an effective amount of at least two different therapeutic substances, wherein the first therapeutic substance is a CSA and the second therapeutic substance is an antifungal.

Some embodiments further comprise administering an expectorant.

Some embodiments further comprise administering a medication that loosens secretions.

Some embodiments further comprise administering a medication that loosens secretions, wherein the medication that loosens secretions is dornase alfa or hypotonic saline and the secretion is mucus or sputum.

Some embodiments further comprise administering a medication that loosens secretions, wherein the medication that loosens secretions is a deoxyribonuclease enzyme or saline and the secretion is mucus or sputum.

In some embodiments, the CSA further reduces lung inflammation mediated by a tumor necrosis factor.

In some embodiments, the CSA further reduces lung scarring.

In some embodiments, the CSA is selected by measuring a biomarker or subjecting a sample from the patient to a companion diagnostic device in the patient.

In some embodiments, the biomarker is a cellular response to the CSA or the companion diagnostic device measures a cellular response to the CSA.

In some embodiments, the cellular response is a change in mRNA levels associated with inflammation.

In some embodiments, the patient is a mammal.

In some embodiments, the mammal is a human.

Some embodiments are directed to a pharmaceutical composition comprising a therapeutically effective amount of at least one cationic steroid antimicrobial (CSA), or a pharmaceutically acceptable salt thereof and a pharmaceutically acceptable excipient, wherein the composition is suitable for inhalation.

DETAILED DESCRIPTION OF THE PREFERRED EMBODIMENTS

Figure 1A:
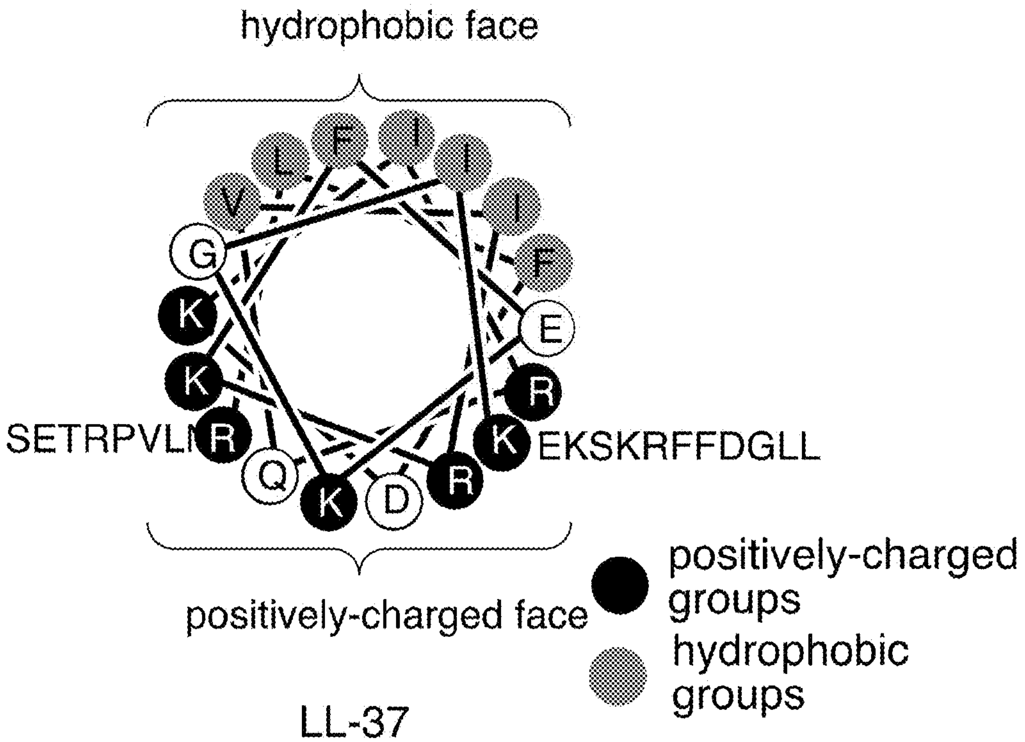
FIGS. 1A and 1B illustrate a comparison of cathelicidin LL-37 (FIG. 1A) and a representative cationic steroidal antimicrobial (CSA) (FIG. 1).
Figure 1B:
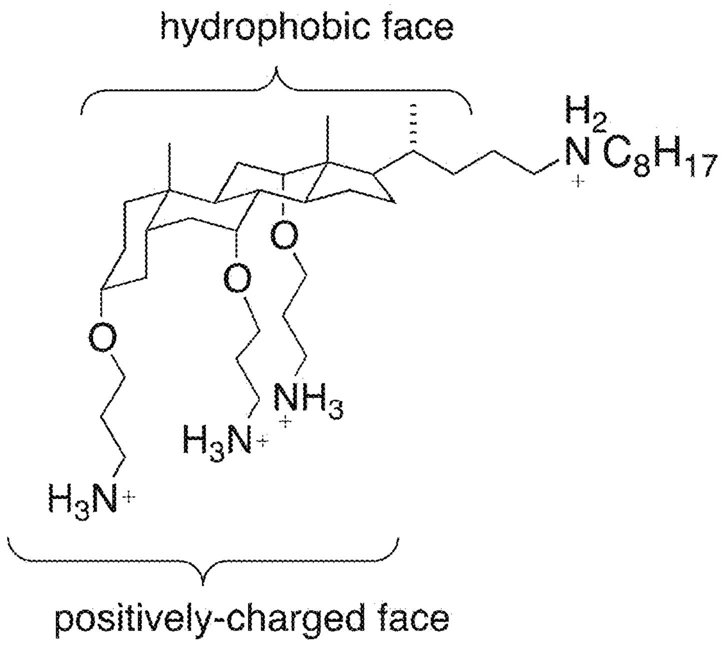

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

Definitions

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms “a,” “an,” and “the” are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term ‘including’ should be read to mean “including, without limitation,” “including but not limited to,” or the like; the term “comprising” as used herein is synonymous with “including,” “containing,” or “characterized by,” and is inclusive or open-ended and does not exclude additional, unrecited elements or method steps; the term “having” should be interpreted as “having at least;” the term “includes” should be interpreted as “includes but is not limited to;” the term “example” is used to provide exemplary instances of the item in discussion, not an exhaustive or limiting list thereof; and use of terms like “preferably,” “preferred,” “desired,” or “desirable,” and words of similar meaning should not be understood as implying that certain features are critical, essential, or even important to the structure or function of the invention, but instead as merely intended to highlight alternative or additional features that may or may not be utilized in a particular embodiment. In addition, the term “comprising” is to be interpreted synonymously with the phrases “having at least” or “including at least”. When used in the context of a process, the term “comprising” means that the process includes at least the recited steps, but may include additional steps. When used in the context of a compound, composition or device, the term “comprising” means that the compound, composition or device includes at least the recited features or components, but may also include additional features or components. Likewise, a group of items linked with the conjunction “and” should not be read as requiring that each and every one of those items be present in the grouping, but rather should be read as “and/or” unless expressly stated otherwise. Similarly, a group of items linked with the conjunction “or” should not be read as requiring mutual exclusivity among that group, but rather should be read as “and/or” unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ represent substituents that can be attached to the indicated atom. Unless otherwise specified, an R group may be substituted or unsubstituted.

A "ring" as used herein can be heterocyclic or carbocyclic. The term "saturated" used herein refers to a ring having each atom in the ring either hydrogenated or substituted such that the valency of each atom is filled. The term "unsaturated" used herein refers to a ring where the valency of each atom of the ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$ $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, 0-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R^aO(CH_2)_mO—$, $R^b(CH_2)_nO—$, $R^cC(O)O(CH_2)_pO—$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "Ca" or "Ca to C" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3—$, $CH_3CH_2—$, $CH_3CH_2CH_2—$, $(CH_3)_2CH—$, $CH_3CH_2CH_2CH_2—$, $CH_3CH_2CH(CH_3)—$ and $(CH_3)_3C—$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkenyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkynyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as $—CH_2—$ tethering groups, forming bonds to connect molecular fragments via their terminal carbon atoms. Examples include but are not limited to methylene ($—CH_2—$), ethylene ($—CH_2CH_2—$), propylene ($—CH_2CH_2CH_2—$), and butylene ($—CH_2CH_2CH_2CH_2—$). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —$NH_2$ group.

As used herein, the term "hydroxy" refers to a —OH group.

A "cyano" group refers to a "—CN" group.

A "carbonyl" or an "oxo" group refers to a C═O group.

The term "azido" as used herein refers to a —$N_3$ group.

As used herein, "aminoalkyl" refers to an amino group connected, as a substituent, via a lower alkylene group. Examples include $H_2N$-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(═O)O-alkyl- and alkyl-O—C(═O)-alkyl- with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

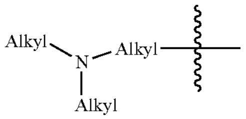

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include $H_2N$-alkyl-O— and $H_2N$-alkoxy with the terms alkyl and alkoxy as defined herein.

As used herein, "aminoalkyloxyalkyl" refers to an amino group connected, as a substituent, to an alkyloxy group connected, as a substituent, to an alkyl group. Examples include $H_2N$-alkyl-O-alkyl- and $H_2N$-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include $H_2N$-alkyl-C(═O)O— and $H_2N$-alkyl-O—C(═O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include $H_2N$-alkyl-NH—C(═O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include $H_2N$-alkyl-C(═O)—NH— with the term alkyl as defined herein.

As used herein, "azidoalkyloxy" refers to an azido group connected as a substituent, to an alkyloxy group. Examples include $N_3$-alkyl-O— and $N_3$-alkoxy- with the terms alkyl and alkoxy as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

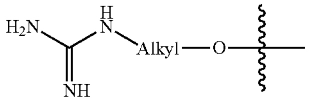

and

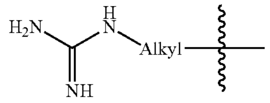

with the terms alkyl and alkoxy as defined herein.X

As used herein, "guanidinoalkylcarboxy" refers to a guanidinyl group connected, as a substituent, to an alkyl group connected, as a substituent, to a carboxy group. Examples include

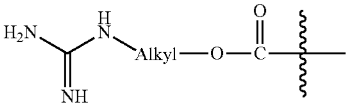

and

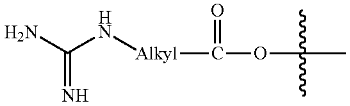

with the term alkyl as defined herein.

As used herein, "quaternaryammoniumalkylcarboxy" refers to a quaternized amino group connected, as a substituent, to an alkyl group connected, as a substituent, to a carboxy group. Examples include

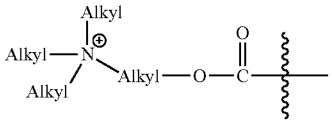

and

-continued

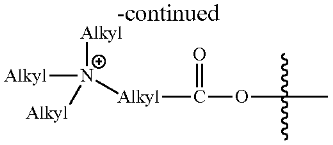

with the term alkyl as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example, "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is $(C_1-C_{10})$ alkyloxy-$(C_1-C_{10})$ alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethyl-carbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl, monomethoxytrityl (MMTr), 4,4'-dimethoxytrityl (DMTr), 4,4',4"-trimethoxytrityl (TMTr), and those described herein).

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

Compounds:

Compounds useful in accordance with this disclosure are described herein, both generically and with particularity, and in U.S. Pat. Nos. 6,350,738, 6,486,148, 6,767,904, 7,598,234, 7,754,705, 8,691,252, 10,676,501, 8,975,310, 9,546,195, 8,932,614, 8,945,217, 8,784,857, 9,533,063, 9,943,614, 9,155,746, 9,694,019, 9,161,942, 9,603,859, 9,314,472, 9,943,529, 10,195,215, 11,524,015, and 9,387,215; U.S. Pat. Pub. Nos. 2013/0236619, 2013/0280391, 2014/0274913, 2016/0311850, 2021/0355155, 2021/0363174, and 2021/0379091; and U.S. Pat. App. No. 61/786,301, which are incorporated herein by reference. Additional compounds and generally and specifically described in relation to the methods discussed herein. The skilled artisan will recognize the compounds within the generic formula set forth herein and understand their preparation in view of the references cited herein and the Examples.

Methods and Uses:

It has been discovered that CSAs can be formulated for inhalation administration and retain useful anti-pathogenic properties that are useful for treating lung infections. Moreover, it has been discovered that such administration is effective against drug-resistant pathogenic strains. As such, the administration of CSAs via inhalation into the lung(s) is particularly suitable for treating lung infections in patients suffering from cystic fibrosis, COPD, tuberculosis, pneumonia, ventilator-assisted pneumonia (VAP), influenza, anthrax, idiopathic pulmonary fibrosis, asthma, etc. Additionally, it has been discovered that the administration of CSAs via inhalation into the lung(s) results in a reduction of lung inflammation, which is a symptom of many lung diseases, including both cystic fibrosis and COPD. Moreover, CSA administration will reduce lung scarring associated with lung infections and COPD. The methods described herein further utilize these remarkable properties of CSAs.

Some embodiments are directed to a method of treating a lung infection with a cationic steroidal antimicrobial (CSA), comprising administering to a lung via inhalation into the lung a therapeutically effective amount of an anti-pathogenic substance comprising at least one cationic steroid antimicrobial (CSA), or a pharmaceutically acceptable salt thereof, to a patient in need of treatment, wherein the CSA administration treats the lung infection. In some embodiments, the method may further comprise identifying a patient in need of treatment for a lung infection. Some embodiments are directed to a method of treating a patient who has been diagnosed as having a lung infection, comprising administering to a lung via inhalation into the lung a therapeutically effective amount of an anti-pathogenic substance comprising at least one cationic steroid antimicrobial (CSA), or a pharmaceutically acceptable salt thereof, to the patient in need of treatment, wherein the CSA administration treats the lung infection.

Some embodiments are directed to a method of reducing lung inflammation with a cationic steroidal antimicrobial (CSA), comprising administering to a lung via inhalation into the lung a therapeutically effective amount of a therapeutic substance comprising at least one cationic steroid antimicrobial (CSA), or a pharmaceutically acceptable salt thereof, to a patient in need of treatment, wherein the CSA administration treats the lung inflammation. In some embodiments, the method may further comprise identifying a patient in need of treating for lung inflammation. Some embodiments are directed to a method of treating a patient who has been diagnosed as having lung inflammation, comprising administering to a lung via inhalation into the lung a therapeutically effective amount of at least one cationic steroid antimicrobial (CSA), or a pharmaceutically acceptable salt thereof, to the patient in need of treatment, wherein the CSA administration treats the lung inflammation.

Some embodiments are directed to a method of treating both a lung infection and lung inflammation with a cationic steroidal antimicrobial (CSA), comprising administering to a lung via inhalation into the lung a therapeutically effective amount of at least one cationic steroid antimicrobial (CSA), or a pharmaceutically acceptable salt thereof, to a patient in need of treatment, wherein the CSA administration treats both the lung infection and lung inflammation. In some embodiments, the method may further comprise identifying a patient in need of treatment for both a lung infection and lung inflammation. In some embodiments, the CSA administration further reduces lung scarring, infection, and/or inflammation.

The lung infection and/or lung inflammation may be from a bacterial lung infection. They may also be from a chronic lung infection and/or chronic lung infection that results in lung inflammation. The lung infection and/or lung inflammation may also be from a drug-resistant infection. In particular, the lung infection and/or lung inflammation may result from antibiotic-resistant infection. In some embodiments, the treated lung infection and/or lung inflammation results from a tobramycin-resistant infection. In some embodiments, the treated lung infection and/or lung inflammation results from a vancomycin-resistant infection. In some embodiments, the treated lung infection and/or lung inflammation results from a methicillin-resistant infection.

In some embodiments, the patient has cystic fibrosis. In some embodiments, the patient has chronic obstructive pulmonary disease. In some embodiments, the patient also suffers from additional ailments, such as lung infections and associated diseases and symptoms. In some embodiments, the patient may also have allergic broncho-pulmonary aspergillosis. Such an infection can be in addition to cystic fibrosis or COPD. In some embodiments, the CSA further reduces lung scarring in such patients.

In some embodiments, the patient's lung infection and/or lung inflammation is caused by *Staphylococcus, Haemophilus, Pseudomonas, Burkholderia, Aspergillus, Scedosporium, Candida, Exophiala, Penicillium*, or *Acrophialophora* pathogens. In some embodiments, the patient's lung infection and/or lung inflammation is caused by one or more of *Staphylococcus aureus, Haemophilus influenzae, Pseudomonas aeruginosa, Burkholderia cepacia, Aspergillus fumigatus, Aspergillus flavus, Aspergillus nidulans, Aspergillus terreus, Scedosporium apiospermum, Scedosporium prolificans, Candida albicans, Exophiala dermatitidis, Penicillium emersonii*, or *Acrophialophora fusispora* pathogens. In some embodiments, the lung infection is caused by *Pseudomonas aeruginosa*, multi-drug resistant *Pseudomonas aeruginosa, Staphylococcus aureus*, methicillin resistant *Staphylococcus aureus, Stenotrophomonas maltophilia*, or *Haemophilus* influenza. In some embodiments, the lung infection is caused by VISA, hVISA, VRSA (MIC 1 mg/L) or CN Staph (MIC 0.03-0.125 mg/L). In some embodiments, the lung infection is caused by a fungus, such as *Candida albicans, Candida albicans* (fluconazole-resistant), *Candida glabrata* (fluconazone-resistant), or *Penicillium*. In some embodiments, the lung infection and/or lung inflammation is the result of a biofilm in the lungs. Accordingly, in some embodiments CSA are administered to reduce the formation or extent of a biofilm.

In some embodiments, one or more, two or more, or three or more CSAs are administered that affect inflammation. For example, in some embodiments, one or more, two or more, or three or more CSAs are administered to reduce lung inflammation. CSAs having anti-inflammatory properties against one or more proteins or signaling pathways can be determined can be determined as described in the Examples below. In some embodiments, the lung inflammation is mediated by an interleukin. In other embodiments, the lung inflammation is mediated by a tumor necrosis factor.

Reduction can be a 5%, 10%, 15%, 20%, 25%, 30%, 35%, 40%, 45%, 50%, 55%, 60%, 65%, 70%, 755, 80%, 85%, 90%, 95%, 99%, or essentially complete reduction in inflammation or infection, or about any of the aforementioned numbers, or a range bounded by any two of the aforementioned numbers. Such values for reduction apply herein regardless of the symptom being referred to, and the values are equally applicable in reference to the phrases "treating," "preventing," "inhibiting," and the like. For example, in some embodiments the pathogen infection or the pathogen burden is reduced by 5%, 10%, 15%, 20%, 25%, 30%, 35%, 40%, 45%, 50%, 55%, 60%, 65%, 70%, 755, 80%, 85%, 90%, 95%, 99%, 99.9%, 99.99% or about any of the aforementioned numbers, or a range bounded by any two of the aforementioned numbers.

In some embodiments, the CSA is a compound of Formula (I), or a pharmaceutically acceptable salt thereof:

(I)

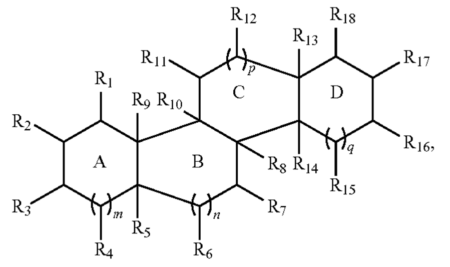

where, rings A, B, C, and D are independently saturated, or are fully or partially unsaturated, provided that at least two of rings A, B, C, and D are saturated;

m, n, p, and q are independently 0 or 1;

$R_1$ through $R_4$, $R_6$, $R_7$, $R_1$, $R_{12}$, $R_{15}$, $R_{16}$, and $R_{18}$ are independently selected from the group consisting of hydrogen, hydroxyl, substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylaminoalkylamino, substituted or unsubstituted aminoalkyl, a substituted or unsubstituted aryl, substituted or unsubstituted arylaminoalkyl, substituted or unsubstituted haloalkyl, substituted or unsubstituted alkenyl, substituted or unsubstituted alkynyl, oxo, linking group attached to a second steroid, substituted or unsubstituted aminoalkyloxy, substituted or unsubstituted aminoalkyloxyalkyl, substituted or unsubstituted aminoalkylcarboxy, substituted or unsubstituted aminoalkylaminocarbonyl, substituted or unsubstituted aminoalkylcarboxamido, substituted or unsubstituted di(alkyl)aminoalkyl, $H_2N$—$HC(Q_5)$—C(O)—O—, $H_2N$—$HC(Q_5)$—C(O)—N(H)—, substituted or unsubstituted azidoalkyloxy, substituted or unsubstituted cyanoalkyloxy, P.G.-HN—$HC(Q_5)$—C(O)—O—, substituted or unsubstituted guanidinoalkyloxy, substituted or unsubstituted quaternary ammonium alkylcarboxy, and substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, substituted or unsubstituted alkyl, substituted or unsubstituted hydroxyalkyl, substituted or unsubstituted alkyloxyalkyl, substituted or unsubstituted aminoalkyl, substituted or unsubstituted aryl, substituted or unsubstituted haloalkyl, substituted or unsubstituted alkenyl, substituted or unsubstituted alkynyl, oxo, linking group attached to a second steroid, substituted or unsubstituted aminoalkyloxy, substituted or unsubstituted aminoalkylcarboxy, substituted or unsubstituted aminoalkylaminocarbonyl, substituted or unsubstituted di(alkyl)aminoalkyl, $H_2N$—$HC(Q_5)$—C(O)—O—, $H_2N$—$HC(Q_5)$—C(O)—N(H)—, azidoalkyloxy, cyanoalkyloxy, P.G.-HN—$HC(Q_5)$—C(O)—O—, guanidinoalkyloxy, and guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of substituted or unsubstituted aminoalkyl, substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, substituted or unsubstituted aminoalkylcarboxy, substituted or unsubstituted arylaminoalkyl, substituted or unsubstituted aminoalkyloxyaminoalkylaminocarbonyl, substituted or unsubstituted aminoalkylaminocarbonyl, substituted or unsubstituted aminoalkylcarboxamido, quaternary ammonium alkylcarboxy, substituted or unsubstituted di(alkyl)aminoalkyl, $H_2N$—$HC(Q_5)$—C(O)—O—, $H_2N$—$HC(Q_5)$—C(O)—N(H)—, azidoalkyloxy, cyanoalkyloxy, P.G.-HN—$HC(Q_5)$—C(O)—O—, substituted or unsubstituted guanidinoalkyloxy, and substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, substituted or unsubstituted ($C_1$-$C_{22}$) alkyl, substituted or unsubstituted ($C_1$-$C_{22}$) hydroxyalkyl, substituted or unsubstituted ($C_1$-$C_{22}$) alkyloxy-($C_1$-$C_{22}$) alkyl, substituted or unsubstituted ($C_1$-$C_{22}$) alkylcarboxy-($C_1$-$C_{22}$) alkyl, substituted or unsubstituted ($C_1$-$C_{22}$) alkylamino-($C_1$-$C_{22}$)alkyl, substituted or unsubstituted ($C_1$-$C_{22}$) alkylamino-($C_1$-$C_{22}$) alkylamino, substituted or unsubstituted ($C_1$-$C_{22}$) alkylamino-($C_1$-$C_{22}$) alkylamino-($C_1$-$C_{22}$) alkylamino, substituted or unsubstituted ($C_1$-$C_{22}$) aminoalkyl, substituted or unsubstituted aryl, substituted or unsubstituted arylamino-($C_1$-$C_{22}$) alkyl, substituted or unsubstituted ($C_1$-$C_{22}$) haloalkyl, substituted or unsubstituted $C_2$-$C_6$ alkenyl, substituted or unsubstituted $C_2$-$C_6$ alkynyl, oxo, linking group attached to a second steroid, substituted or unsubstituted ($C_1$-$C_{22}$) aminoalkyloxy, substituted or unsubstituted ($C_1$-$C_{22}$) aminoalkyloxy-($C_1$-$C_{22}$) alkyl, substituted or unsubstituted ($C_1$-$C_{22}$) aminoalkylcarboxy, substituted or unsubstituted ($C_1$-$C_{22}$) aminoalkylamino-carbonyl, substituted or unsubstituted ($C_1$-$C_{22}$) aminoalkylcarboxamido, substituted or unsubstituted di($C_1$-$C_{22}$ alkyl)aminoalkyl, $H_2N$—$HC(Q_5)$—C(O)—O—, $H_2N$—HC ($Q_5$)—C(O)—N(H)—, substituted or unsubstituted ($C_1$-$C_{22}$) azidoalkyloxy, substituted or unsubstituted ($C_1$-$C_{22}$) cyanoalkyloxy, P.G.-HN $HC(Q_5)$—C(O)—O—, substituted or unsubstituted ($C_1$-$C_{22}$) guanidinoalkyloxy, substituted or unsubstituted ($C_1$-$C_{22}$) quaternary ammonium alkylcarboxy, and substituted or unsubstituted ($C_1$-$C_{22}$) guanidinoalkylcarboxy, where $Q_5$ is a side chain of an amino acid (including a side chain of glycine, i.e., H), and P.G. is an amino protecting group;

$R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, substituted or unsubstituted ($C_1$-$C_{22}$) alkyl, substituted or unsubstituted ($C_1$-$C_{22}$) hydroxyalkyl, substituted or unsubstituted ($C_1$-$C_{22}$) alkyloxy-($C_1$-$C_{22}$) alkyl, substituted or unsubstituted ($C_1$-$C_{22}$) aminoalkyl, substituted or unsubstituted aryl, substituted or unsubstituted ($C_1$-$C_{22}$) haloalkyl, substituted or unsubstituted ($C_2$-$C_6$) alkenyl, substituted or unsubstituted ($C_2$-$C_6$) alkynyl, oxo, linking group attached to a second steroid, substituted or unsubstituted ($C_1$-$C_{22}$) aminoalkyloxy, substituted or unsubstituted ($C_1$-$C_{22}$) aminoalkylcarboxy, substituted or unsubstituted ($C_1$-$C_{22}$) aminoalkylaminocarbonyl, substituted or unsubstituted di($C_1$-$C_{22}$ alkyl) aminoalkyl, $H_2N$—$HC(Q_5)$—C(O)O—, $H_2N$—$HC(Q_5)$—C (O)—N(H)—, substituted or unsubstituted ($C_1$-$C_{22}$) azidoalkyloxy, substituted or unsubstituted ($C_1$-$C_{22}$) cyanoalkyloxy, P.G.-HN—$HC(Q_5)$—C(O)—O—, substituted or unsubstituted ($C_1$-$C_{22}$) guanidinoalkyloxy, and substituted or unsubstituted ($C_1$-$C_{22}$) guanidinoalkylcarboxy, where $Q_5$ is a side chain of any amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of substituted or unsubstituted ($C_1$-$C_{22}$) aminoalkyl, substituted or unsubstituted ($C_1$-$C_{22}$) aminoalkyloxy, substituted or unsubstituted ($C_1$-$C_{22}$) alkylcarboxy-($C_1$-$C_{22}$) alkyl, substituted or unsubstituted ($C_1$-$C_{22}$) alkylamino-($C_1$-$C_{22}$) alkylamino, substituted or unsubstituted ($C_1$-$C_{22}$) alkylamino-($C_1$-$C_{22}$) alkylamino ($C_1$-$C_{22}$) alkylamino, substituted or unsubstituted ($C_1$-$C_{22}$) aminoalkylcarboxy, substituted or unsubstituted arylamino ($C_1$-$C_{22}$) alkyl, substituted or unsubstituted ($C_1$-$C_{22}$) aminoalkyloxy ($C_1$-$C_{22}$) aminoalkylaminocarbonyl, substituted or unsubstituted ($C_1$-$C_{22}$) aminoalkylaminocarbonyl, substituted or unsubstituted ($C_1$-$C_{22}$) aminoalkylcarboxyamido, substituted or unsubstituted ($C_1$-$C_{22}$) quaternary ammonium alkylcarboxy, substituted or unsubstituted di($C_1$-$C_{22}$ alkyl)aminoalkyl, $H_2N$—HC ($Q_5$)—C(O)—O—, $H_2N$—$HC(Q_5)$—C(O)—N(H)—, substituted or unsubstituted ($C_1$-$C_{22}$) azidoalkyloxy, substituted or unsubstituted ($C_1$-$C_{22}$) cyanoalkyloxy, P.G.-HN—HC($Q_5$)—C(O)—O—, substituted or unsubstituted ($C_1$-$C_{22}$) guanidinoalkyloxy, and substituted or unsubstituted ($C_1$-$C_{22}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, unsubstituted ($C_1$-$C_{18}$) aminoalkyl, unsubstituted aryl, unsubstituted arylamino-($C_1$-$C_{18}$) alkyl, oxo, unsubstituted ($C_1$-$C_{18}$) aminoalkyloxy, unsubstituted ($C_1$-$C_{18}$) aminoalkyloxy-($C_1$-$C_{18}$) alkyl, unsubstituted ($C_1$-$C_{18}$) aminoalkylcarboxy, unsubstituted ($C_1$-$C_{18}$) aminoalkylaminocarbonyl, unsubstituted ($C_1$-$C_{18}$) aminoalkylcarboxamido, unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy;

$R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, unsubstituted ($C_1$-$C_{18}$) aminoalkyl, unsubstituted aryl, an unsubstituted arylamino-($C_1$-$C_{18}$) alkyl, oxo, unsubstituted ($C_1$-$C_{18}$) aminoalkyloxy, unsubstituted ($C_1$-$C_{18}$) aminoalkyloxy-($C_1$-$C_{18}$) alkyl, unsubstituted ($C_1$-$C_{18}$) aminoalkylcarboxy, unsubstituted ($C_1$-$C_{18}$) aminoalkylaminocarbonyl, unsubstituted ($C_1$-$C_{18}$) aminoalkylcarboxamido, unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, unsubstituted ($C_1$-$C_{18}$) aminoalkyl, unsubstituted aryl, unsubstituted arylamino-($C_1$-$C_{18}$) alkyl, oxo, unsubstituted ($C_1$-$C_{18}$) aminoalkyloxy, unsubstituted ($C_1$-$C_{18}$) aminoalkyloxy-($C_1$-$C_{18}$) alkyl, unsubstituted ($C_1$-$C_{18}$) aminoalkylcarboxy, unsubstituted ($C_1$-$C_{18}$) aminoalkylaminocarbonyl, unsubstituted ($C_1$-$C_{18}$) aminoalkylcarboxamido, unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

In some embodiments, m, n, and p, are each 1 and q is 0 such that the CSA is a compound of Formula (IA), or a pharmaceutically acceptable salt thereof:

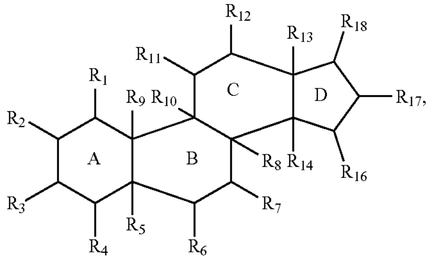

(IA)

where, rings A, B, C, and D are independently saturated, or are fully or partially unsaturated, provided that at least two of rings A, B, C, and D are saturated; and $R_1$ through $R_{14}$ and $R_{16}$ through $R_{15}$ can be as above for Formula I.

In some embodiments, $R_3$, $R_7$, $R_{12}$, and $R_{15}$ are independently selected from the group consisting of hydrogen, unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, unsubstituted ($C_1$-$C_{18}$) aminoalkyl, unsubstituted arylamino-($C_1$-$C_{18}$) alkyl, unsubstituted ($C_1$-$C_{18}$) aminoalkyloxy, unsubstituted ($C_1$-$C_{18}$) aminoalkyloxy-($C_1$-$C_{18}$) alkyl, unsubstituted ($C_1$-$C_{18}$) aminoalkylcarboxy, unsubstituted ($C_1$-$C_{18}$) aminoalkylaminocarbonyl, unsubstituted ($C_1$-$C_{18}$) aminoalkylcarboxamido, unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{15}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, unsubstituted ($C_1$-$C_{16}$) aminoalkyl, unsubstituted arylamino-($C_1$-$C_5$) alkyl, unsubstituted ($C_1$-$C_5$) aminoalkyloxy, unsubstituted ($C_1$-$C_{16}$) aminoalkyloxy-($C_1$-$C_5$) alkyl, unsubstituted ($C_1$-$C_5$) aminoalkylcarboxy, an unsubstituted ($C_1$-$C_5$) aminoalkylaminocarbonyl, unsubstituted ($C_1$-$C_5$) aminoalkyl-carboxamido, unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

In some embodiments, $R_1$, $R_2$, $R_4$, $R_5$, $R_6$, $R_5$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{15}$ are independently selected from the group consisting of substituted or unsubstituted aminoalkyloxy, substituted or unsubstituted aminoalkylcarboxy, substituted or unsubstituted alkylaminoalkyl, substituted or unsubstituted alkoxycarbonylalkyl, substituted or unsubstituted alkylcarbonylalkyl, substituted or unsubstituted di(alkyl)aminoalkyl, substituted or unsubstituted alkylcarboxyalkyl, and substituted or unsubstituted hydroxyalkyl.

In some embodiments, $R_3$, $R_7$, and $R_{12}$ are independently selected from the group consisting of substituted or unsubstituted aminoalkyloxy and substituted or unsubstituted aminoalkylcarboxy; and $R_{15}$ is selected from the group consisting of substituted or unsubstituted alkylaminoalkyl, substituted or unsubstituted alkoxycarbonylalkyl, substituted or unsubstituted alkylcarbonyloxyalkyl, substituted or unsubstituted di(alkyl)aminoalkyl, substituted or unsubstituted alkylaminoalkyl, substituted or unsubstituted alkyloxycarbonylalkyl, substituted or unsubstituted alkylcarboxyalkyl, and substituted or unsubstituted hydroxyalkyl.

In some embodiments, $R_3$, $R_7$, and $R_{12}$ are the same. In some embodiments, $R_3$, $R_7$, and $R_{12}$ are substituted or unsubstituted aminoalkyloxy. In some embodiments, $R_3$, $R_7$, and $R_{12}$ are substituted or unsubstituted aminoalkylcarboxy. In some embodiments, $R_{15}$ is substituted or unsubstituted alkylaminoalkyl. In some embodiments, $R_{15}$ is substituted or unsubstituted alkoxycarbonylalkyl. In some embodiments, $R_{15}$ is substituted or unsubstituted di(alkyl)aminoalkyl. In some embodiments, $R_{15}$ is substituted or unsubstituted alkylcarboxyalkyl. In some embodiments, $R_{15}$ is substituted or unsubstituted hydroxyalkyl.

In some embodiments, $R_3$, $R_7$, $R_{12}$, and $R_{15}$ are independently selected from the group consisting of amino-$C_3$-alkyloxy; amino-$C_3$-alkyl-carboxy; amino-$C_2$-alkylcarboxy; $C_8$-alkylamino-$C_5$-alkyl; $C_8$-alkoxy-carbonyl-$C_4$-alkyl; $C_{10}$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; $C_{16}$-alkylamino-$C_5$-alkyl; $C_{12}$-alkylamino-$C_5$-alkyl; and hydroxy($C_5$)alkyl.

In some embodiments, the CSA, or a pharmaceutically acceptable salt thereof, is selected from the compound of Formula (IB):

(IB)

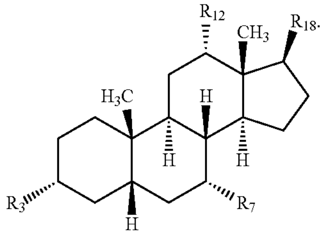

The substituents for $R_3$, $R_7$, $R_{12}$ and $R_{18}$ in Formula IB can be any of the substituents for $R_3$, $R_7$, $R_{12}$ and $R_{18}$ above for Formula I and Formula 1A.

In some embodiments, the CSA of Formula (IB), or a pharmaceutically acceptable salt thereof, is at least one CSA selected from the group consisting of:

(CSA-8)

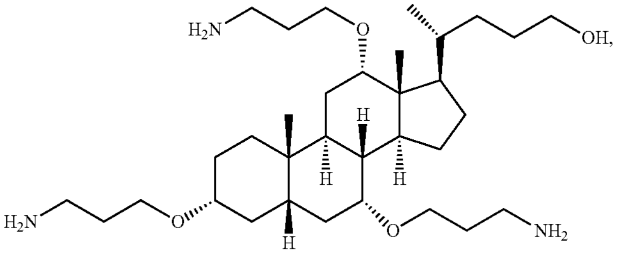

(CSA-13)

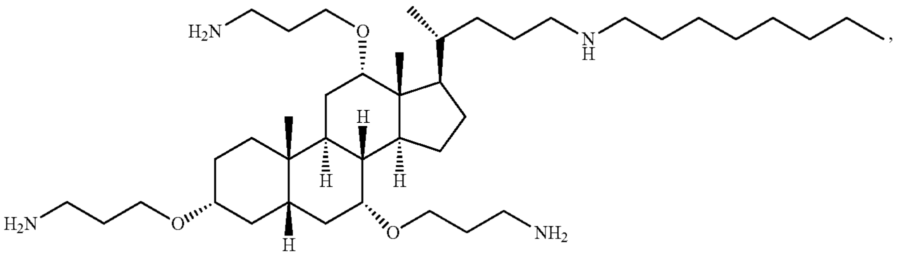

(CSA-44)

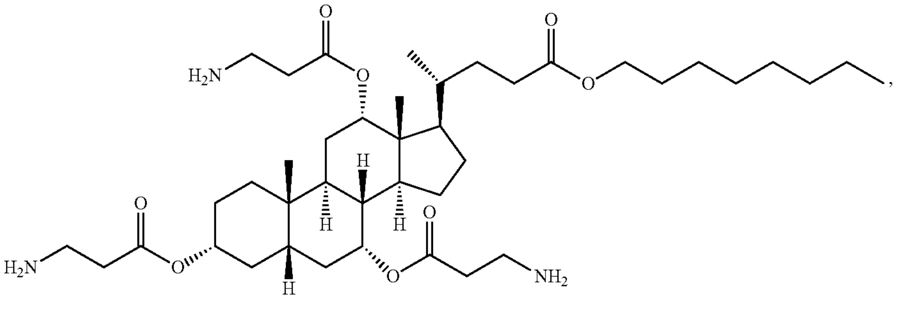

-continued
(CSA-90)
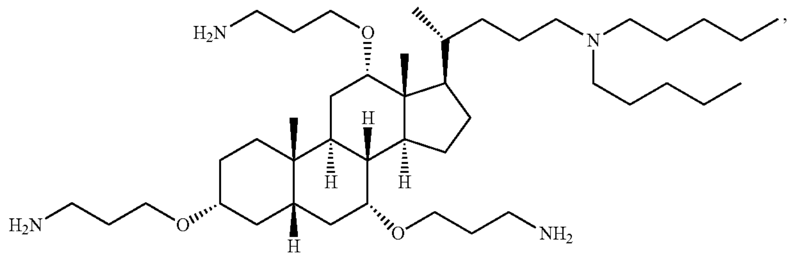
(CSA-135)
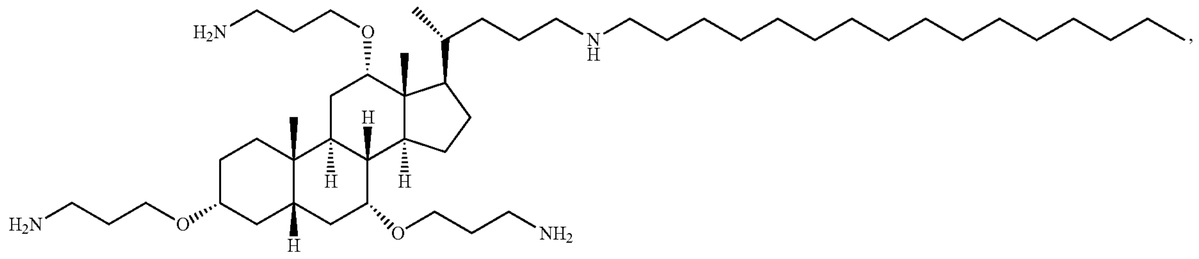
(CSA-131)
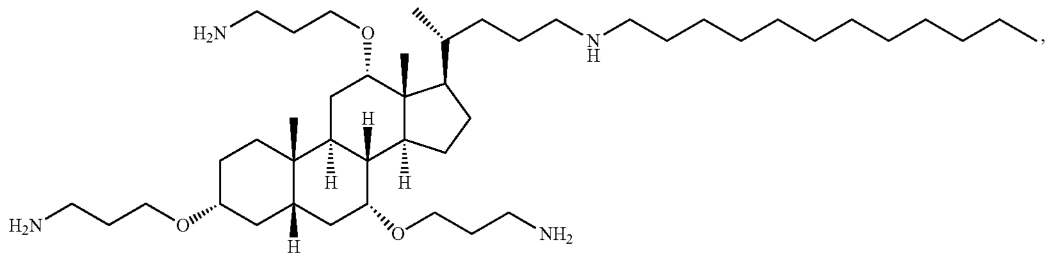
(CSA-134)
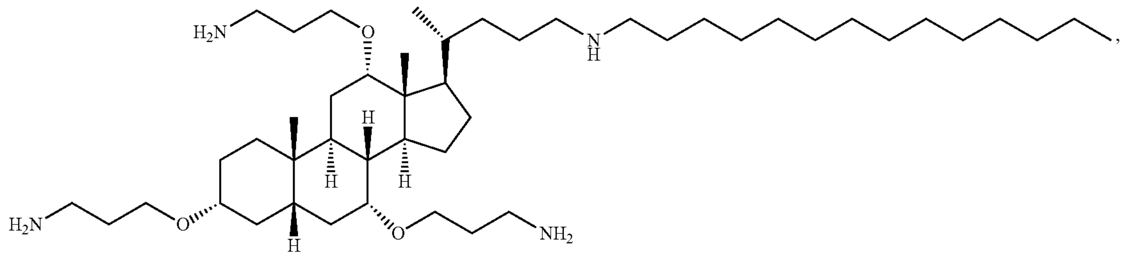
(CSA-136)
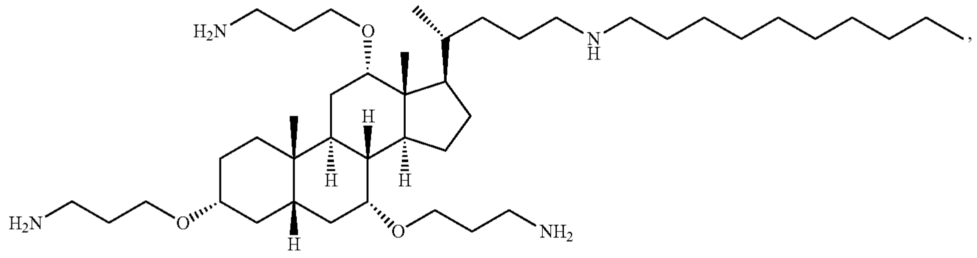
(CSA-137)
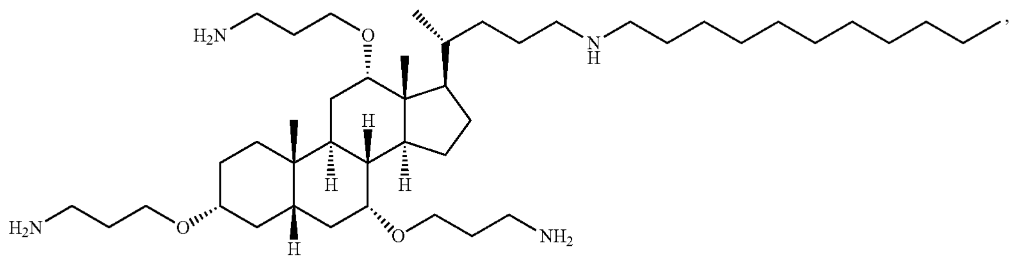

-continued (CSA-138)

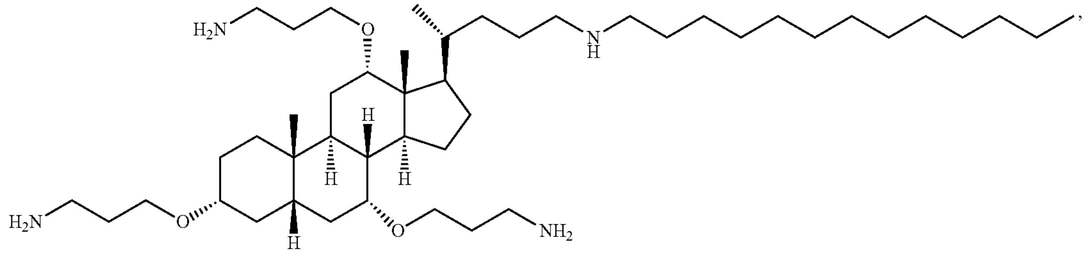

(CSA-142)

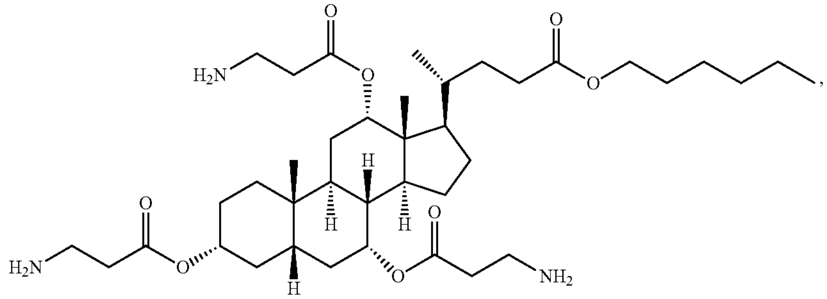

(CSA-144)

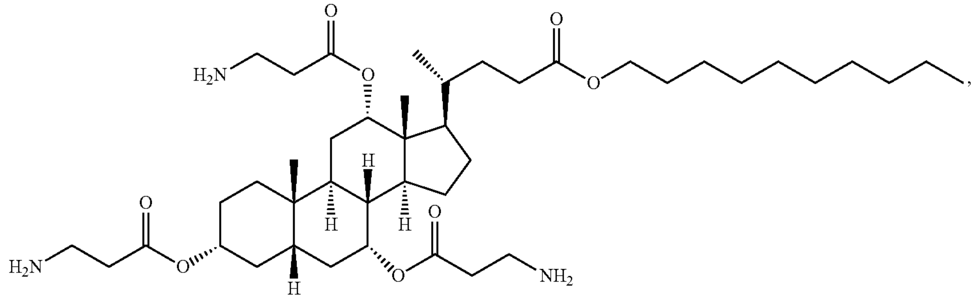

(CSA-145)

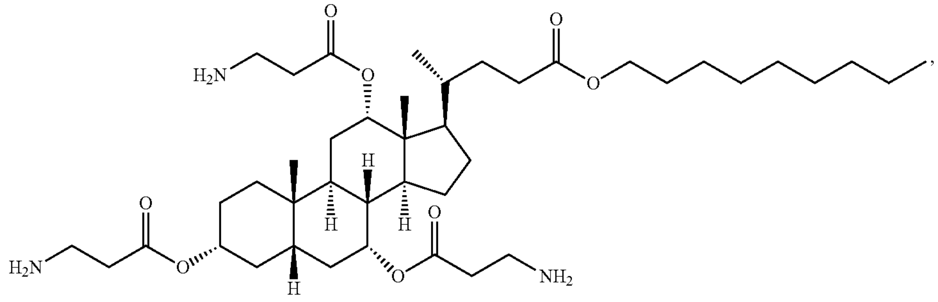

, and (CSA-146)

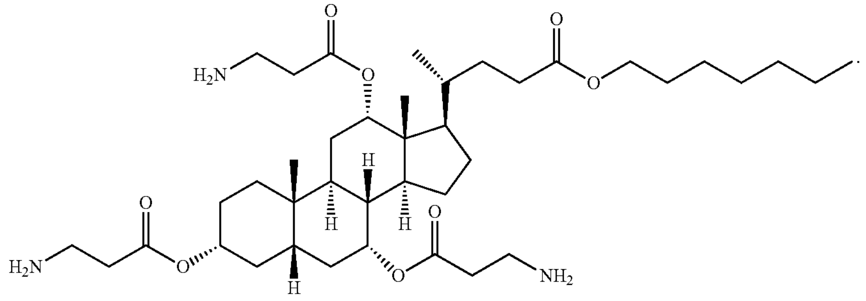

In some embodiments, such as any of the ones described herein, CSA-13 is excluded as a species.

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt. Additional pharmaceutically acceptable salts are described herein.

In some embodiments, the CSA is selected by measuring a biomarker or subjecting a sample from the patient to a companion diagnostic device in the patient. In some embodiments, the biomarker is a cellular response to the CSA or the companion diagnostic device measures a cellular response to the CSA. In some embodiments, the cellular response is a change in mRNA levels associated with inflammation.

In some embodiments, the therapeutic effect of the CSA is derived from its steroid-like structure. In other embodiments, the therapeutic effect of the CSA is derived from its antibiotic activity. In some embodiments, the therapeutic effect of the CSA is derived from a combination of antibiotic and anti-inflammatory activity. In some embodiments, the therapeutic effect of the CSA is derived from a modulation of NFKB or a tumor necrosis factor.

Pharmaceutically Acceptable Salts

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt. In some embodiments, the pharmaceutically acceptable salt is a sulfate salt. In other embodiments, the pharmaceutically acceptable salt is a monosulfate salt. In other embodiments, the pharmaceutically acceptable salt is a 1,5-dinapthalenesulphonic acid salt. In other embodiments, the pharmaceutically acceptable salt is a 1,5-naphthalenedisulfonic acid salt.

Co-Administration:

In some embodiments, one or more CSAs or a therapeutic substance are co-administered. In other embodiments, the co-administration accounts for the therapeutic benefit. In some embodiments, co-administration is concurrent (within less than 1 minute of the first administration).

In some embodiments, one or more CSAs or a therapeutic substance are sequentially administered (administered one after the other). Examples of sequential administration include administering one substance followed by beginning the administration of a second substance within 24 hours, 20 hours, 16 hours, 12 hours, 8 hours, 4 hours, 1 hour, 30 minutes, 15 minutes, 5 minutes, 1 minute, a range bounded by any two of the aforementioned numbers, and/or about any of the aforementioned numbers. In some embodiments, the sequential administration accounts for the therapeutic benefit.

In some embodiments, one or more non-CSA anti-inflammatory agents are administered to the patient. In some embodiments, the one or more non-CSA anti-inflammatory agents are co-administered. Such agents include, but are not limited to, a regulatory agency approved anti-inflammatory agent. In some embodiments, the regulatory agency is the Food and Drug Administration (FDA). In other embodiments, the anti-inflammatory agent is a non-steroidal anti-inflammatory agent ("NSAID") such as aspirin, diclofenac, ibuprogen, naproxen, rofecoxib, and the like. In some embodiments, acetaminophen is administered with the CSA. In other embodiments, the anti-inflammatory agent is a steroidal anti-inflammatory agent such as prednisone or prednisolone.

In some embodiments, the method of treatment further comprises administering an effective amount of at least two different therapeutic substances. In some embodiments, the two different therapeutic substances are two different anti-pathogenic substances. In some embodiments, the administration is concurrent. In other embodiments, the administration is sequential. In some embodiments, an effective amount of at least two different therapeutic substances are administered. In some embodiments, both therapeutic substances are CSAs. In some embodiments both therapeutic substances are administered to a lung via inhalation into the lung. In some embodiments, a first therapeutic substance that is a CSA is administered and a second therapeutic substance is a non-CSA antibiotic is administered. Some embodiments further comprise administering an effective amount of at least two different therapeutic substances, wherein the first therapeutic substance is a CSA and the second therapeutic substance is an antibiotic selected from the group consisting of an aminoglycoside, an ansamycin, a carbacephem, a carbapenem, a cephalosporin, a glycopeptide, a lincosamide, a lipopeptide, a macrolide, a monbactam, a nitrofuran, an oxazolidonone, a penicillin, a polypeptide, a quinolone, a sulfonamide, and a tetracycline. In some embodiments, the first therapeutic substance is a CSA and the second therapeutic substance is tobramycin, colistin, aztreonam, ciprofloxacin, azithromycin, erythromycin, or vancomycin. In some embodiments, the first therapeutic substance is a CSA and the second therapeutic substance is an antifungal. In some embodiments, the antifungal is an "azole" antifungal. In some embodiments, the first therapeutic substance is a CSA and the second therapeutic substance is an antiviral. In some embodiments, the antiviral is oseltamivir. In some embodiments, an expectorant is administered. In some embodiments, an anti-mucolytic is administered. In some embodiments, the anti-mucolytic is erdosteine, acetylcysteine, bromheksin, carbocysteine, guiafenesin, or iodinated glycerol. In some embodiments, a medication that loosens secretions is administered. In some embodiments, the medication that loosens secretions is dornase alfa or hypotonic saline and the secretion is mucus or sputum. In some embodiments, the medication that loosens secretions is a deoxyribonuclease enzyme or saline and the secretion is mucus or sputum. One or both of the substances can be administered via inhalation, one or both of the substances can be administered concurrently, or one or both substances can be administered sequentially.

Inhalation

Some embodiments are directed to a pharmaceutical composition comprising a therapeutically effective amount of at least one cationic steroid antimicrobial (CSA), or a pharmaceutically acceptable salt thereof, and a pharmaceutically acceptable excipient, wherein the composition is suitable for inhalation into a patient's lung(s). Formulations, e.g., for parenteral or oral administration, are most typically solids, liquid solutions, emulsions or suspensions, while inhalable formulations for pulmonary administration (i.e., inhalation into the lung(s)) are generally liquids or powders, with powder formulations being generally preferred. In some embodiments, at least one CSA is administered to the patient via inhalation. In other embodiments, all CSAs are administered to the patient via inhalation into the lung(s). In some embodiments, all therapeutic substances given to the patient for treatment of the specified condition are given to the patient via inhalation. A skilled artisan will readily appreciate suitable dosage forms (tablet, capsule, injectable) and routes of administration (oral, parenteral, IV) when not administering via inhalation.

In some embodiments, the CSAs and/or additional therapeutic substances are formulated as aerosols for administration to the patient. Aerosols are preparations packaged under pressure and contain therapeutic agent(s) and a propellant that are released upon activation of an appropriate valve system. Upon activation of the valve system, the drug substance is released as a plume of fine particles or droplets. Generally, one dose is released from the preparation upon activation of a metered valve. In some embodiments, however, the patient or prescribing physician can adjust the amount administered.

Typical components of aerosols are the formulation containing one or more drug substances and propellant, the container, the valve, and the actuator. Aerosol preparations may consist of either a two-phase (gas and liquid) or a three-phase (gas, liquid, and solid or liquid) formulation. In some embodiments, the two-phase formulation consists of drug(s) dissolved in liquefied propellant. In some embodiments, liquid cosolvents, such as water, alcohol, propylene glycol, and polyethylene glycols are added. In some embodiments, liquid cosolvents are added to enhance the solubility of the CSA or additional therapeutic drug substance(s). Some embodiments are directed to three phase inhalation and/or nasal aerosol systems. In some embodiments, three phase inhalation and nasal aerosol systems consist of a suspension or emulsion of the CSA and/or additional therapeutic substances in addition to the vaporizable propellants. The suspension or emulsion of the finely divided drug substance typically is dispersed in the liquid propellant with the aid of suitable biocompatible surfactants or other excipients. Propellants for aerosol formulations are generally low molecular weight hydrofluorocarbons or hydrocarbons that are liquid when constrained in the container, exhibit a suitable vapor pressure at room temperature, and are biocompatible and nonirritating.

In one embodiment, the aerosol includes particles and/or liquid droplets capable of being suspended in air for a period of time ranging from 5 seconds 10 seconds, 30 seconds, 1 minute, 5 minutes, 10 minutes, 15 minutes, 30 minutes, 1 hour, or greater. In one embodiment, either the droplet size or the particle size should be small enough that the aerosol can remain suspended in air long enough to be distributed in a space (e.g., a room, a ventilation system, a body cavity, etc.). Preferably, the particles or droplets in the aerosols described herein have a lower size range of 0.001, 0.01, 0.1, 0.2, 0.3, 0.4, 0.5, 0.6, 0.7, 0.8, 0.9, or 1 micron in diameter, an upper size range of 5, 10, 15, 20, 25, 30, 35, 40, 45, or 50 microns, or any combination of the above listed lower and upper size ranges.

In some embodiments, the CSAs and/or additional therapeutic substances are formulated as dry powders. Such powders are useful for administering with dry powder inhalers. In some embodiments, the dry powder inhaler (DPI) consists of a mixture of CSA and/or additional therapeutic substances and carrier, and all components exist in a finely divided solid state. Such can also be packaged as a unit dose. When using a dry powder inhaler, the dose is released from the packaging by an appropriate mechanism and is mobilized into a fine mist upon oral inhalation by the patient.

Typical components of the DPI are the formulation consisting of the CSA and/or additional therapeutic substances and carrier, both in the dry state; packaging that contains an amount equivalent to a unit dose; and a mechanism designed to open the unitdose container and permit mobilization of the powders by the patient inhaling through a mouthpiece, generally a the built-in mouthpiece. Typically, the unit-dose container is either a capsule made of gelatin or other suitable non-animal-derived material (e.g., hypromellose or starch), or the container may consist of a series of unit doses in foil-lined blisters arranged in a strip. In some embodiments, such as when the CSA and/or additional therapeutic substances is contained in a capsule, release of the medication takes place when the capsule is pierced. As a consequence of this release mechanism, a skilled artisan will understand that the device is designed to minimize the generation of capsule fragments that might subsequently be inhaled. In some embodiments, such as when the CSA and/or additional therapeutic substances is contained in a blister pack, the mechanism is designed to advance an unused blister to a platform where the foil lining can be peeled back to expose the powder mixture to an air stream created when the patient inhales. In some embodiments, to facilitate dosing compliance, some delivery devices incorporate dosing administration information such as the number of doses remaining.

In some embodiments, the CSAs and/or additional therapeutic substances are formulated as a spray for inhalation. A spray is a preparation that contains the CSAs and/or additional therapeutic substances in either the liquid or solid state. In some embodiments, the spray is intended for administration as a fine mist of small aqueous droplets. The droplets may be generated by means other than the use of a volatile propellant, for example as described above with respect to aerosols. In some embodiments, spray formulations (especially those intended for nasal or oral inhalation) have an aqueous base. Nasal preparations may be solutions, suspensions, or emulsions intended for local or systemic effect. In some embodiments, the sprays are isotonic. In some embodiments, the sprays may contain excipients to control pH and viscosity. In some embodiments, liquid sprays are generated from solutions by nebulization. In some embodiments, nebulization creates an approximately continuous generation of a fine mist of droplets from a drug-containing solution. Nebulization can apply the Venturi principle, ultrasonic energy, or other suitable mechanical methods for droplet generation. In some embodiments, the generated mist is directed to the patient for inhalation, and can be further accommodated with an appropriate tube or face mask. In some embodiments, the formulation for nebulization is a solution. In other embodiments, the formulation for nebulization is a suspension or emulsions. In some embodiments, the CSAs and/or additional therapeutic substances are formulated as a suspension for inhalation. A suspension is a biphasic preparation consisting of solid particles dispersed throughout a liquid phase. In some embodiments, suspensions are prepared by adding suspending agents or other excipients and purified water or oil to solid therapeutic substances and mixing to achieve uniformity. Surfactants, alcohol, glycerin, and other hydrophilic liquids can be employed as wetting agents when an aqueous vehicle will be used as the dispersion phase. In some embodiments, preservatives are included in the formulation to protect against bacteria and mold contamination. In some embodiments, suspensions are shaken before the administration.

Pharmaceutical Excipients

While it is possible for the compounds described herein to be administered alone, it may be preferable to formulate the compounds as pharmaceutical compositions (i.e., formulations). As such, in yet another aspect, pharmaceutical compositions useful in the methods and uses of the disclosed embodiments are provided. A pharmaceutical composition is any composition that may be administered in vitro or in vivo or both to a subject in order to treat or ameliorate a condition. In a preferred embodiment, a pharmaceutical composition may be administered by inhalation in vivo as described above. In some exemplary embodiments, the subject is an animal. In some embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-pathogenic, anti-bacterial, anti-fungal, or anti-microbial agents).

Formulations may contain one or more excipients. Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

The pharmaceutical compositions may also be in the form of oil-in water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

To obtain a stable water-soluble dose form of a pharmaceutical composition, a pharmaceutically acceptable salt of a compound described herein may be dissolved in an aqueous solution. The aqueous solution may contain a physiologically compatible buffer, or an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

Many therapeutics have undesirably short half-lives and/or undesirable toxicity. Thus, the concept of improving half-life or toxicity is applicable to various treatments and fields. Pharmaceutical compositions can be prepared, however, by complexing the therapeutic with a biochemical moiety to improve such undesirable properties. Proteins are a particular biochemical moiety that may be complexed with a CSA for administration in a wide variety of applications. In some embodiments, one or more CSAs are complexed with a protein to improve half-life or toxicity. Albumin is a particularly preferred protein for complexation with a CSA. In some embodiments, the albumin is fat-free albumin.

With respect to the CSA therapeutic, the biochemical moiety for complexation can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the weight ratio of albumin to CSA is about 18:1 or less, such as about 9:1 or less. In some embodiments, the CSA is coated with albumin.

Alternatively, or in addition, non-biochemical compounds can be added to the pharmaceutical compositions to reduce the toxicity of the therapeutic and/or improve the half-life. Suitable amounts and ratios of an additive that can reduce toxicity can be determined via a cellular assay. With respect to the CSA therapeutic, toxicity reducing compounds can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the toxicity reducing compound is a cocoamphodiacetate such as Miranol® (disodium cocoamphodiacetate). In other embodiments, the toxicity reducing compound is an amphoteric surfactant. In some embodiments, the toxicity reducing compound is a surfactant. In other embodiments, the molar ratio of cocoamphodiacetate to CSA is between about 8:1 and 1:1, preferably about 4:1. In some embodiments, the toxicity reducing compound is allantoin.

In some embodiments, a CSA composition is prepared utilizing one or more surfactants. In specific embodiments, the CSA is complexed with one or more poloxamer surfactants. Poloxamer surfactants are nonionic triblock copolymers composed of a central hydrophobic chain of polyoxypropylene (poly(propylene oxide)) flanked by two hydrophilic chains of polyoxyethylene (poly(ethylene oxide)). In some embodiments, the poloxamer is a liquid, paste, or flake (solid). Examples of suitable poloxamers include those by the trade names Synperonics, Pluronics, or Kolliphor. In some embodiments, one or more of the poloxamer surfactant in the composition is a flake poloxamer. In some embodiments, the one or more poloxamer surfactant in the composition has a molecular weight of about 3600 g/mol for the central hydrophobic chain of polyoxypropylene and has about 70% polyoxyethylene content. In some embodiments, the ratio of the one or more poloxamer to CSA is between about 50 to 1; about 40 to 1; about 30 to 1; about 20 to 1; about 10 to 1; about 5 to 1; about 1 to 1; about 1 to 10; about 1 to 20; about 1 to 30; about 1 to 40; or about 1 to 50. In other embodiments, the ratio of the one or more poloxamer to CSA is between 50 to 1; 40 to 1; 30 to 1; 20 to 1; 10 to 1; 5 to 1; 1 to 1; 1 to 10; 1 to 20; 1 to 30; 1 to 40; or 1 to 50. In some embodiments, the ratio of the one or more poloxamer to CSA is between about 50 to 1 to about 1 to 50. In other embodiments, the ratio of the one or more poloxamer to CSA is between about 30 to 1 to about 3 to 1. In some embodiments, the poloxamer is Pluronic F127.

The amount of poloxamer may be based upon a weight percentage of the composition. In some embodiments, the amount of poloxamer is about 10%, 15%, 20%, 25%, 30%, 35%, 40%, about any of the aforementioned numbers, or a range bounded by any two of the aforementioned numbers or the formulation. In some embodiments, the one or more poloxamer is between about 10% to about 40% by weight of a formulation administered to the patient. In some embodiments, the one or more poloxamer is between about 20% to about 30% by weight of the formulation. In some embodiments, the formulation contains less than about 50%, 40%, 30%, 20%, 10%, 5%, or 1% of CSA, or about any of the aforementioned numbers. In some embodiments, the formulation contains less than about 20% by weight of CSA.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA comprises a multimer (e.g., a dimer, trimer, tetramer, or higher order polymer). In some exemplary embodiments, the CSAs can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Dosages

Compounds (e.g., CSAs) can be administered in accordance with the methods at any frequency as a single dose or multiple dose, e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects and the therapeutic indication. Alternatively, dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, a dose of between 0.01 mg and 3000 mg of the active ingredient, preferably between 1 mg and 700 mg, e.g., 5 to 200 mg. The dosage may preferably depend upon the body weight of the patient. For example, the dosage may be between 0.01 mg/kg and 3000 mg/kg of the active ingredient, preferably between 1 mg/kg and 700 mg/kg, e.g. 5 to 200 mg/g or 20 to 100 mg/kg. The dosage may be a single one or a series of two or more given in the course of one or more days, as is needed by the subject. In some embodiments, the compounds will be administered for a period of continuous therapy, for example for a week or more, or for months or years. Doses tailored for particular types of the diseases or symptoms described herein, or for particular patients, can be selected based, in part, on the $GI_{50}$, TGI, $LC_{50}$ and/or MIC values that are either known or readily measured, such as according to the Examples.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). For example, therapeutic dosages may result in plasma levels of 0.05 μg/mL, 0.1 μg/mL, 0.5 μg/mL, 1 μg/mL, 5 μg/mL, 10 μg/mL, 15 μg/mL, 20 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, 100 μg/mL, a range bounded by any two of the aforementioned numbers, or about any of the aforementioned numbers and ranges. In some embodiments, the therapeutic dose is sufficient to establish plasma levels in the range of about 0.1 μg/mL to about 10 μg/mL. In other embodiments, the therapeutic dose is sufficient to establish plasma levels in the range of 1 μg/mL to 20 μg/mL. The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Some embodiments are directed to the use of companion diagnostics to identify an appropriate treatment for the patient. A companion diagnostic is an in vitro diagnostic test or device that provides information that is essential for the safe and effective use of a corresponding therapeutic product. Such tests or devices can identify patients likely to be at risk for adverse reactions as a result of treatment with a particular therapeutic product. Such tests or devices can also monitor responsiveness to treatment (or estimate responsiveness to possible treatments). Such monitoring may include schedule, dose, discontinuation, or combinations of therapeutic agents. In some embodiments, the CSA is selected by measuring a biomarker in the patient. The term biomarker includes, but is not limited to, genetic regulation, protein levels, RNA levels, and cellular responses such as cytotoxicity. In some embodiments, one or more CSAs are selected by subjecting a sample from the patient to a companion diagnostic device. In some embodiments, the sample is a tissue sample. In other embodiments, the tissue sample is representative of the area to be treated. In some embodiments, the tissue sample contains a portion of the area to be treated. In some embodiments, the studied biomarker is a cellular response to the CSA or the companion diagnostic device measures a cellular response to the CSA. In some embodiments, the cellular response is a change in mRNA levels associated with inflammation.

EXAMPLES

Synthesis of CSAs:

Compounds described herein can be prepared by known methods, such as those disclosed in U.S. Pat. Nos. 6,350,738, 9,527,883, and 10,370,403, which are incorporated herein by reference. A skilled artisan will readily understand that minor variations of starting materials and reagents may be utilized to prepare known and novel cationic steroidal antimicrobials. For example, the preparation of CSA-13 disclosed in U.S. Pat. No. 6,350,738 (compound 133) can be used to prepare CSA-135 by using hexadecylamine rather than octyl amine as disclosed. A skilled artisan will readily appreciate the synthesis of CSAs from fundamental chemistry principles such as those described in the prior art and those exemplified herein. Schematically, for example, the preparation of certain compounds can be accomplished as follows:

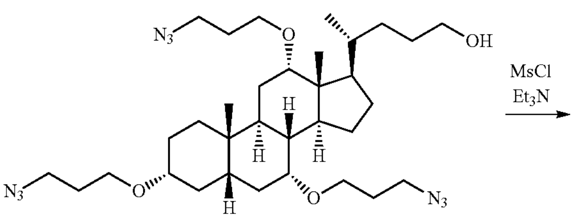

1-A

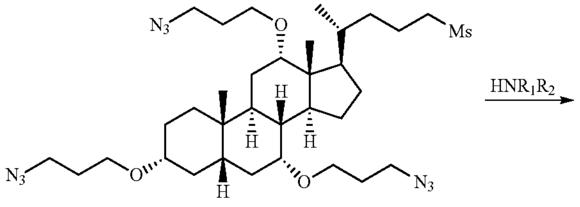

1-B

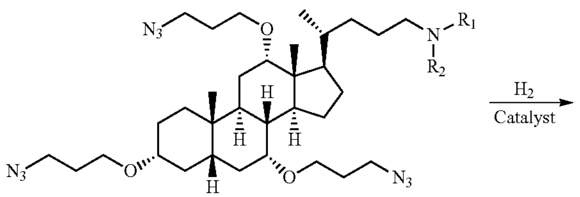

1-C

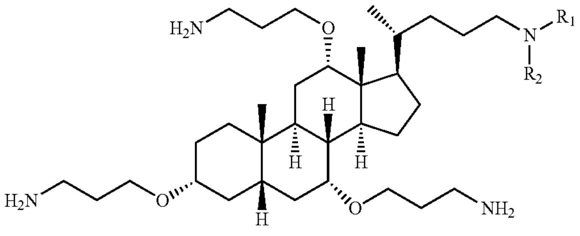

1-D

As shown above, compound 1-A is converted to the mesylate, compound 1-B using known conditions. Treatment of compound 1-B with a secondary amine, such as $HNR_1R_2$, results in the formation of compound 1-C, whose azido functional groups are reduced with hydrogen gas in the presence of a suitable catalyst to afford compound 1-D. Suitable catalysts include Palladium on Carbon and Lindlar catalyst. The reagent $HNR_1R_2$ is not particularly limited under this reaction scheme. For example, when $R_1$ is hydrogen and $R_2$ is a $C_8$-alkyl, CSA-13 is obtained from the synthesis. When $R_1$ is hydrogen and $R_2$ is a $C_{16}$-alkyl, CSA-92 is obtained from the synthesis. When $R_1$ and $R_2$ are both $C_8$-alkyl, CSA-90 is obtained from the synthesis.

Inflammation Gene Regulation

To determine the role of synthetic Ceragenins CSA-13, 44 and 90 in inflammation using mesenchymal stem cells (MSC), targeted mRNA panels from SABiosciences, and primary cells from Lonza were selected. Cells were purchased from Lonza.com and used fresh for each test using recommended media and culture conditions. After treatment, mRNA was isolated using Qiagen RNeasy Mini Kit®, and quantified using a NanoDrop 2000® by UV at 260 nm and 260/280 ratio for purity. cDNA was made using a First Strand Kit® from SABiosciences and processed for real time PCR using a kit from the same company for selected analysis of wound healing pathways. Results from q-PCR were uploaded to the SABiosciences site and to Ingenuity.com web site for analysis and pathway mapping. On day 1, primary human MSC cells were plated at 200,000 cells/well using 6-well plates with 3 ml of recommended media—hMSC Basal Medium+BulletKit (50 ml Growth Supplement, 10 ml L-Glutamine and 0.5 ml Gentamicin Sulfate Amphotercin-B) for 24 hours. Only early passages of cells were used, and never from frozen stock. On day 2, cells were treated with compounds dissolved in DMSO diluted 1:1000 or more to avoid effects of the solvent. Final testing concentration for CSA-13 was 5.0 μM. Treatment lasted 8 hours, and was followed by RNA isolation using QIAGEN RNeasy Mini Kit® (74104). RNA was measured at 260/280 nm using a NanoDrop 2000® and normalized to 2.4 ng per well, cDNA preparation was done using QIAGEN First Strand kit 330401. q-PCR was run as absolute quantification and threshold set at 0.1 units. Dendritic cells were plated at 500,000 cells/well using 24-well plate with 500 ul of Lonza LGM-3 Complete Growth Medium with and without compound. Treatment lasted 8 hours and was followed by RNA isolation using QIAGEN RNeasy Mini Kit® (74104). RNA was measured at 260/280 nm using NanoDrop2000® and normalized to 2.4 ng per well, cDNA preparation was done using QIAGEN First Strand kit 330401. PCR was run as absolute quantification and threshold set at 0.1 units. The results of these experiments are summarized in Tables 1-3 for CSA-13, 44, and 90, respectively. The results highlight the significant modulation of genes related to inflammation, such as IL1A (Interleukin-1 alpha), IL1B (Interleukin-1 beta), TLR2 (Toll-like receptor 2), TLR4 (Toll-like receptor 4), TLR6 (Toll-like receptor 6), TLR8 (Toll-like receptor 8), TLR9 (Toll-like receptor 9), TNF (Tumor necrosis factor), TNFRSF1A (Tmor necrosis factor receptor superfamily member 1A), IRAK2 (Interleukin-1 receptor-associated kinase 2), NFKB1 (Nuclear factor of kappa light polypeptide gene enhancer in B-cells 1), NFKB2 (Nuclear factor of kappa light polypeptide gene enhancer in B-cells 2), and NFKBIA (Nuclear factor of kappa light polypeptide gene enhancer in B-cells inhibitor, alpha). Such results clearly illustrate the potential of CSAs for modulating inflammation.

TABLE 1

Gene Expression Results for CSA-13

| Gene Symbol | Fold Regulation |
|---|---|
| IL1A | −5.5237 |
| IL1B | −16.3901 |
| TLR2 | −7.6418 |
| TLR4 | −2.6139 |
| TLR6 | −4.8417 |
| TLR8 | −2.107 |
| TLR9 | −2.1421 |
| TNF | −8.1805 |
| TNFRSF1A | −5.1031 |
| IRAK2 | −43.5175 |
| NFKB1 | −3.4437 |
| NFKB2 | −4.2155 |
| NFKBIA | −22.966 |

TABLE 2

| Gene Expression Results for CSA-44 | |
|---|---|
| Gene Symbol | Fold Regulation |
| IL1A | −6.0325 |
| IL1B | −28.5329 |
| IRAK2 | −31.8021 |
| NFKB1 | −3.2891 |
| NFKB2 | −2.2766 |
| NFKBIA | −52.206 |
| TLR2 | −15.7179 |
| TLR4 | −2.977 |
| TLR6 | −2.392 |
| TLR8 | −8.2256 |
| TLR9 | −1.8905 |
| TNF | −25.9588 |
| TNFRSF1A | −2.2461 |

TABLE 3

| Gene Expression Results for CSA-90 | |
|---|---|
| Gene Symbol | Fold Regulation |
| IL1A | −6.96 |
| 1L1B | −3.6734 |
| IRAK2 | −52.0069 |
| NFKB1 | −4.718 |
| NFKB2 | −2.5474 |
| NFKBIA | −26.0352 |
| TLR2 | −13.6933 |
| TLR4 | −3.4278 |
| TLR6 | −2.0885 |
| TLR8 | −4.1972 |
| TLR9 | −1.8613 |
| TNF | −4.8514 |
| TNFRSF1A | −7.3196 |

Figure 2:
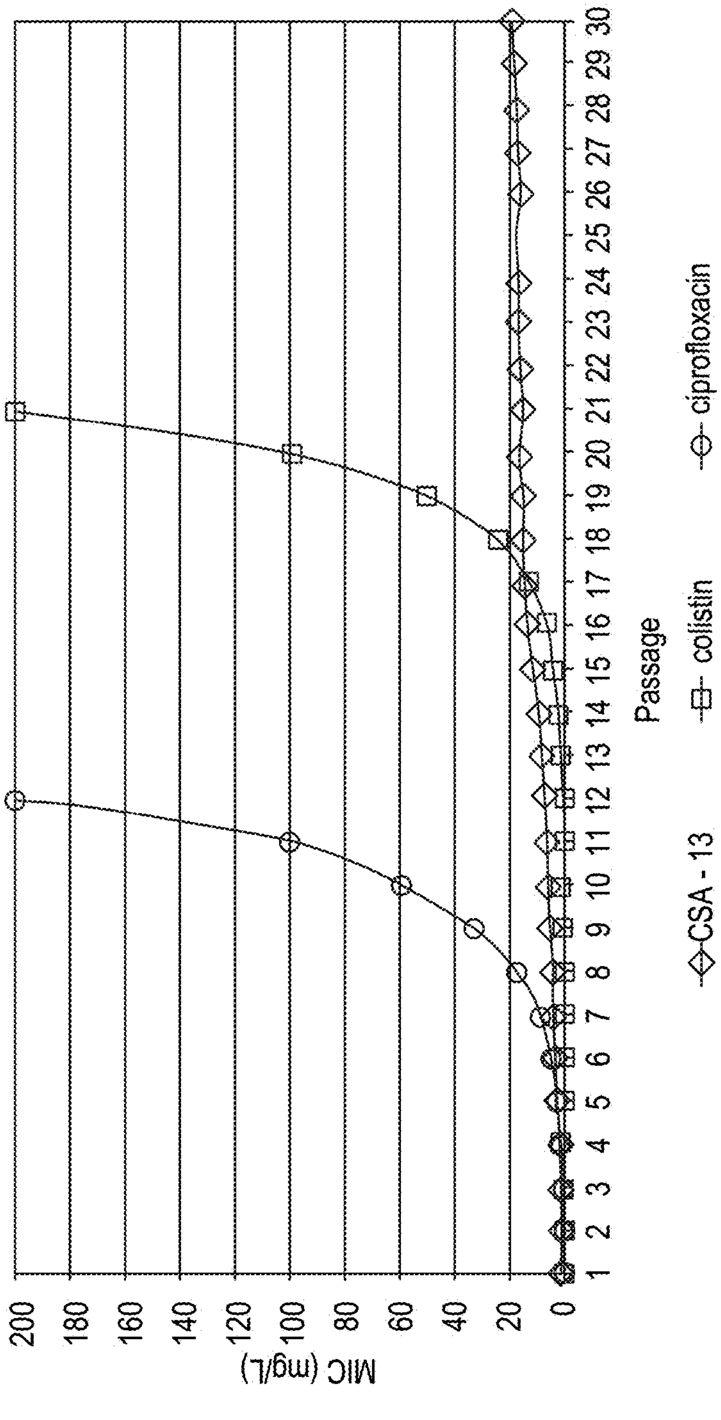
FIG. 2 is a graph comparing Minimum Inhibitory Concentration (MIC) values (in mg/L) for CSA-13, colistin, and ciprofloxacin against *P. aeruginosa* per the number of serial passages.

Assessment of CSA Bacterial Resistance:

A central consideration in the development of novel antimicrobials is potential generation of bacterial resistance. To determine the likelihood of CSA bacterial resistance relative to other "standard" antibiotics, bacteria were serially exposed CSA-13, and MIC values were measured. See Pollard J E, et al. *J. Antimicrob. Chemother.* 2012, 67, 2665-2672 (describing experimental protocol). The results of the trial for CSA-13, colistin, and ciprofloxacin are provided in FIG. 2 for a select bacterium. With *Staphylococcus aureus*, no significant change in Minimum Inhibitory Concentration (MIC) for CSA-13 was observed after 30 serial passages. With *Pseudomonas aeruginosa*, a rise in MIC was observed with CSA-13, and this change was much smaller than those observed with comparators ciprofloxacin and colistin and appeared to level off at 20 μg/mL (FIG. 2). Similar results were also obtained when using antimicrobial peptides instead of CSAs. Interestingly, the results are adaptational rather than mutational, and bacteria revert to fully susceptible forms when outside of the CSA antimicrobial.

Tobramycin Resistant *P. aeuruginisa* Strains:

Tobramycin is commonly used in reducing the bacterial burden in the lungs of cystic fibrosis patients. However, resistance to tobramycin is often observed among *P. aeruginosa* isolates. Tobramycin resistance is typically achieved by acylation or phosphorylation of the primary amine groups in the antibiotic. Because many CSAs, such as CSA-13, contain primary amino groups, an experiment was performed to determine if tobramycin cross-resistance would be observed with CSAs, such as CSA-13.

Figure 3:
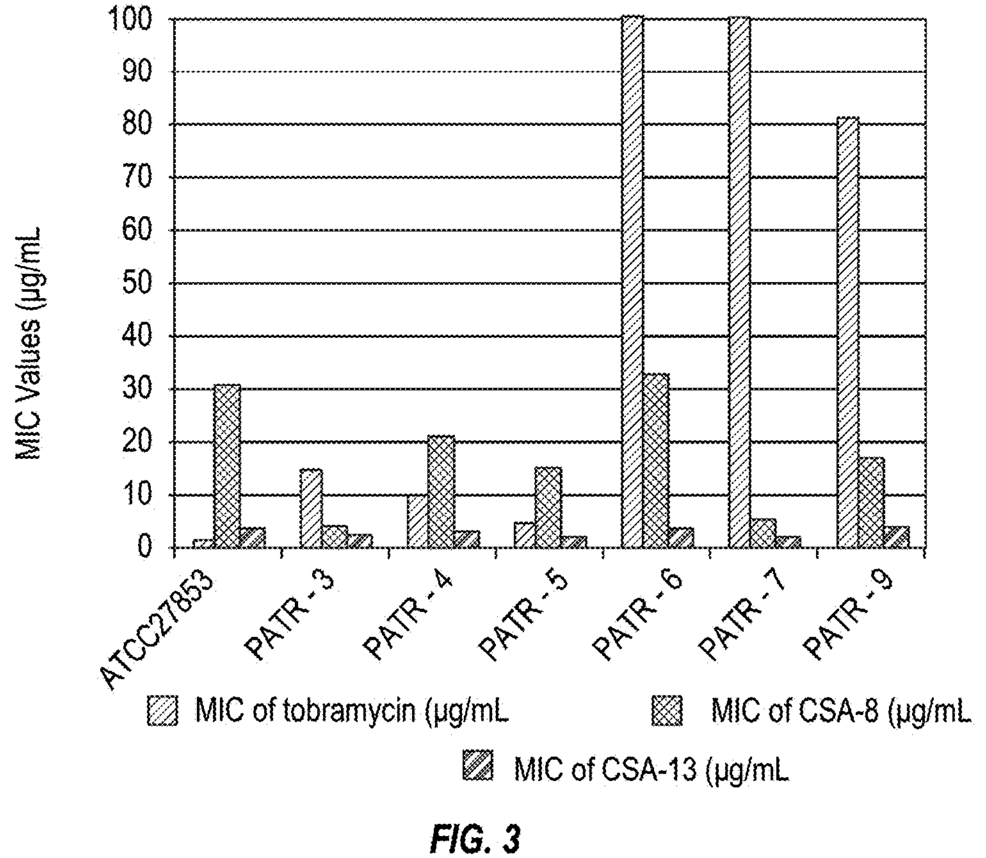
FIG. 3 is a graph comparing Minimum Inhibitory Concentration (MIC) values (in mg/L) for CSA-13, CSA-8, and tobramycin against various tobramycin-resistant *P. aeruginosa* strains.

FIG. 3 provides the results for CSA-13, CSA-8, and tobramycin against seven tobramycin resistant strains. Tobramycin susceptibility varied significantly between the strains, but, unlike for tobramycin, all strains were comparably susceptible to CSA-13. This suggests that no cross resistance is anticipated. Similar studies can be conducted for other drug-resistant pathogenic strains following this standard experimental protocol.

Following the protocols outlined in *Appl. Microbiol. Biotechnol.,* 2010 (September) pp. 251-63 and *Chemotherapy,* 2011 (November), Vol. 57, pp. 505-10, drug combinations involving CSAs and anti-pathogenic substances are performed. In particular, CSA-13 in combination with colistin was evaluated against *P. aeruginosa* and a 54% synergistic result was observed. Additional synergies were observed when combined with tobramycin and ciprofloxaxin, but the synergy observed for the colistin combination was the strongest. Moreover, when CSA-13 was administered with erythromycin, the MIC of erythromycin was reduced 92%.

Animal Model of Lung Infection and Inflammation

In vivo studies were designed to allow observation of both tolerance for CSAs and effectiveness of the antimicrobial in reducing bacterial burden. An infection model was used in which mice were inoculated with *P. aeruginosa* (PAO1) intra-nasally ($10^5$ CFU) to establish an infection. This strain of *Pseudomonas* is susceptible to CSA-13, with an MIC of 2.5 μg/mL. Because many CSAs are readily water soluble, CSA-13 in an aqueous formulation was prepared and introduced via nebulization four hours after initial infection. Two doses were used: 40 and 80 mg/kg. With both doses no adverse effects were observed. After 24 h, the mice were euthanized, and lung tissues were homogenized. Bacterial counts were determined by serial dilution, plating on nutrient agar, incubation, and colony counting. As a comparator, tobramycin was administered via the same route, and *P. aeruginosa* counts were determined.

Figure 4:
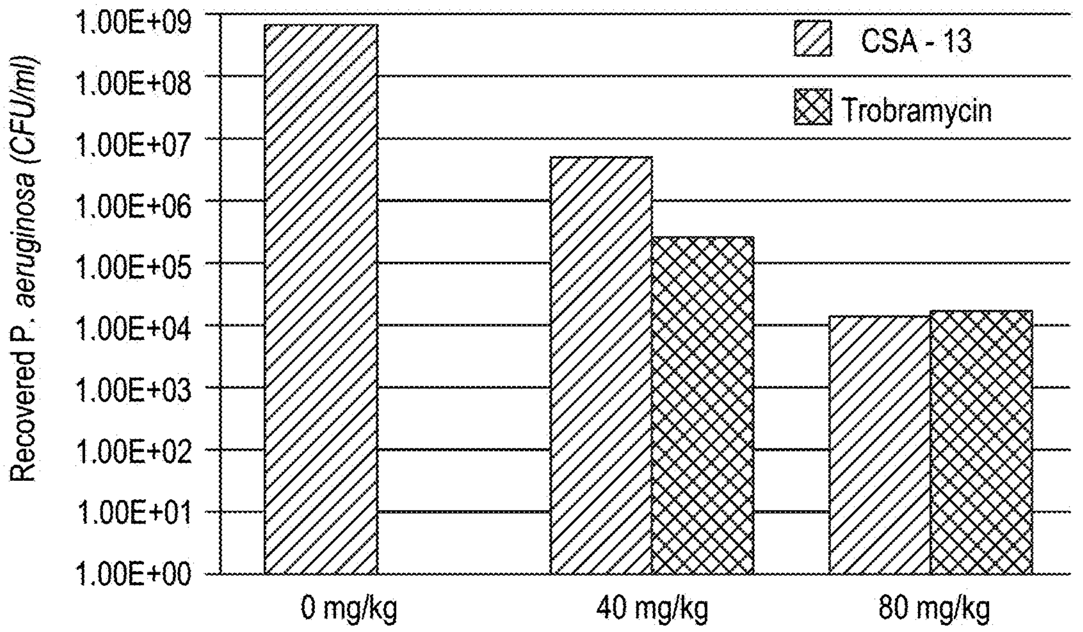
FIG. 4 is a graph comparing Numbers of *P. aeruginosa* (PA01) recovered after treatment with either CSA-13 or tobramycin.
Figure 5:
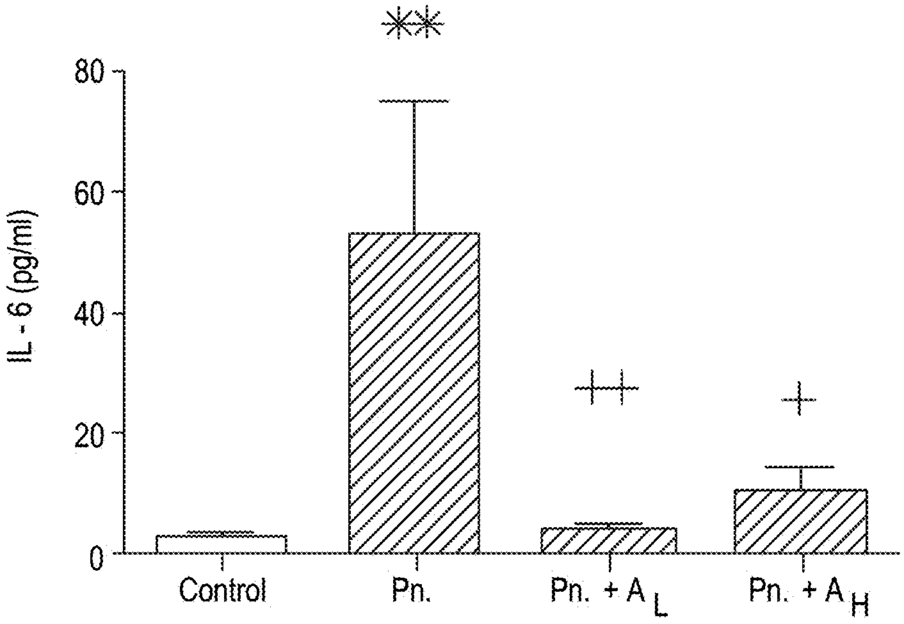
FIG. 5 is a graph illustrating anti-inflammatory and anti-bacterial effect of CSA-13.

The results of this experiment are provided in FIG. 4. A dose-dependent reduction in bacterial counts was observed with both the CSA-13 and tobramycin-treated animals (FIG. 4). With a 40 mg/kg dose, bacterial counts dropped by two logs with CSA-13 and by three logs with tobramycin. At 80 mg/kg, both antimicrobials gave greater than four log reductions in bacterial burden (elimination of 99.99% of the bacterial burden). Moreover, CSA-13 demonstrated efficacy and an anti-inflammatory effect in this murine pneumonia model (See FIG. 5). In FIG. 5, Pn. stands for pneumonia, $A_L$ stands for 40 mg/kg CSA-13 administration, and AH stands for 80 mg/kg CSA-13. IL-6 was measured from kidney tissue specimens. From FIG. 5, it is evident that inhaled CSA-13 reduced *Pseudomonas* load as well as IL-6 levels. CSA-13 efficacy was observed to be comparable to tobramycin against a planktonic PA01 strain.

Figure 6B:
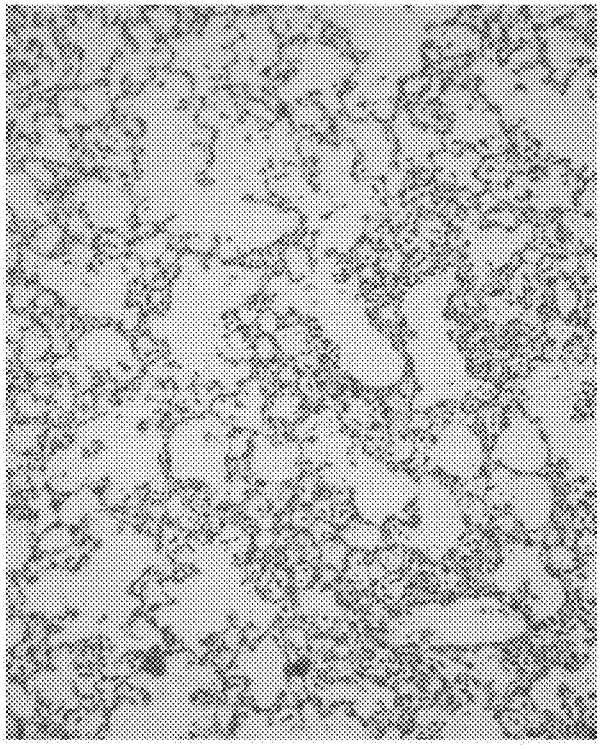
FIGS. 6A and 6B are microscope photographs of lung tissues for comparison of CSA-13 treatment from Murine Lung Histology.
Figure 6A:
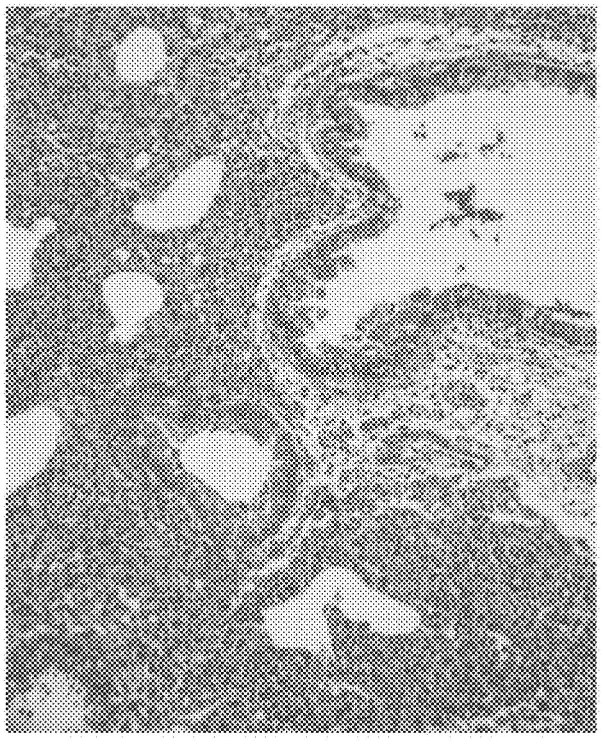

To determine the impact of CSA-13 on murine lungs, histology was performed to observe potential tissue damage (See FIG. 6). In this experiment, mice were infected with $10^8$ PA01 strain of *Pseudomonas*, representing a murine pneumonia model. The picture on the left shows the lung histology for a control animal (no receipt of CSA-13). The picture on the right show the lung histology for an animal that received 80 mg/kg of CSA-13 administered intranasally. The CSA treatment was administered 4 hours post challenge with *Pseudomonas*. The only impacts of CSA-13 administration were to decrease inflammation caused by the infection. In the control group diffuse, severe inflammation was observed, characterized by infiltration of neutrophils. In the lungs of mice receiving the 40 mg/kg dose, a substantial reduction of inflammatory cells around bronchioles in lungs was observed, and an even greater reduction in inflammatory cells was observed in the lungs of the mice receiving the higher (80 mg/kg) dose. Accordingly, CSA-13 was well tolerated and comparably effective to tobramycin in reducing bacterial burden in a mouse model via inhalation administration. Additionally and unexpectedly, an anti-inflammatory effect was observed via this route of administration. Considering the lack of drug resistance observed, the effectiveness of the inhalation route relative to tobramycin, and particularly the anti-inflammatory effect, ceragenins appear well suited both for prevention of bacterial biofilms in the lung and for long-term treatment of lung infections—especially those associated with cystic fibrosis.

In additional experiments, CSAs such as CSA-8, 44, 90, 92, 138, 142, and 144 are formulated as aqueous solutions and administered via the protocol reported above. Some experiments utilize a cocktail (two or more different CSAs) and the therapeutic substances are administered as reported above. Moreover, FDA approved antibiotics and antifungals are solubilized for both concurrent and sequential administration with CSAs and the effects are observed as reported above. In some experiments, the therapeutic substances are prepared in dry powder form and administered via inhalation. Histological studies are performed to determine the in vivo effectiveness of the compounds on the reduction of lung inflammation and/or lung scarring.

Animal Model of COPD:

CSAs are evaluated for their effects on alveolar repair in the rat model of elastase-induced emphysema (Massaro, G. and Massaro, D., Nature, Vol. 3 No. 6: 675-677 (1997)). Animals are divided into treatment groups of approximately eight. Lung inflammation and alveolar damage is induced in male Sprague Dawley rats by a single instillation of pancreatic elastase (porcine derived, Calbiochem) 2 U/gram body mass. Three weeks post injury CSAs are dissolved in an appropriate vehicle of inhalation (water/buffer) at varying concentrations. Animals are treated with CSAs and control groups are challenged with vehicle. In some experiments, CSA combinations and additional therapeutics are evaluated via concurrent and sequential administration. Animals are sacrificed 24 hours after the last dose by exsanguination under deep anesthesia. The lungs are inflated with 10% neutral buffered formalin by intratracheal instillation at a constant rate (1 ml/gram body mass/min). The lung is excised and immersed in fixative for 24 hours prior to processing. Standard methods are used to prepare 5 m paraffin sections. Sections are stained with Hematoxylin and Eosin (H % E). Computerized Morphometric analysis is performed to determine the average alveolar size and alveolar number.

In addition, light micrographs of lung sections are taken. Micrographs are taken of a normal rat lung and a rat lung damaged by elastase and then treated with test compound(s). The micrographs will reveal gross structural differences evident among the lungs receiving the different treatments.

CONCLUSION

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of treating a patient having at least one of a lung infection or lung inflammation with a cationic steroidal antimicrobial (CSA), comprising:

administering via inhalation into a lung of the patient having the at least one of the lung infection or lung inflammation a therapeutically or prophylactically effective amount of the CSA, which provides at least one of antimicrobial or anti-inflammatory activity to treat the at least one of the lung infection or lung inflammation, wherein the CSA is of Formula IB having the following structure, or a pharmaceutically acceptable salt thereof:

(IB)

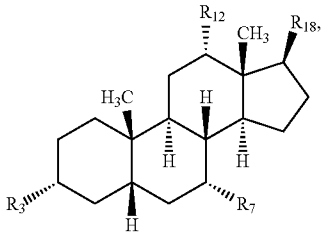

wherein, $R_3$, $R_7$, and $R_{12}$ are independently selected from the group consisting of substituted or unsubstituted aminoalkyloxy and substituted or unsubstituted aminoalkylcarboxyl; and $R_{18}$ is selected from the group consisting of substituted or unsubstituted alkylaminoalkyl; substituted or unsubstituted alkyloxycarbonylalkyl; substituted or unsubstituted alkylcarbonyloxyalkyl; substituted or unsubstituted di(alkyl)-aminoalkyl; substituted or unsubstituted alkylcarboxyalkyl; and substituted or unsubstituted hydroxyalkyl, wherein the CSA is anti-pathogenic with the proviso that the CSA is not CSA-13.

2. The method of claim 1, wherein the patient has at least one of chronic obstructive pulmonary disease (COPD), chronic obstructive lung disease (COLD), chronic obstructive airway disease (COAD), chronic airflow limitation (CAL), chronic obstructive respiratory disease (CORD), or emphysema.

3. The method of claim 1, wherein the patient has cystic fibrosis.

4. The method of claim 3, further comprising administering a medication that loosens secretions, wherein the medication that loosens secretions is dornase alfa, a deoxyribonuclease enzyme, saline, or hypotonic saline and the secretions comprise mucus or sputum.

5. The method of claim 1, wherein the patient has lung inflammation and the CSA reduces lung inflammation mediated by a tumor necrosis factor.

6. The method of claim 1, wherein the patient has a lung infection selected from a bacterial lung infection, a viral lung infection, or a fungal lung infection.

7. The method of claim 1, wherein the CSA is selected from the group consisting of:

(CSA-8)
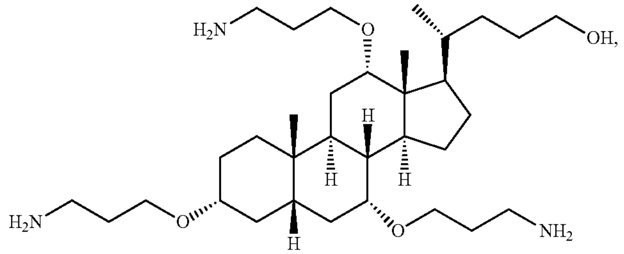
(CSA-44)
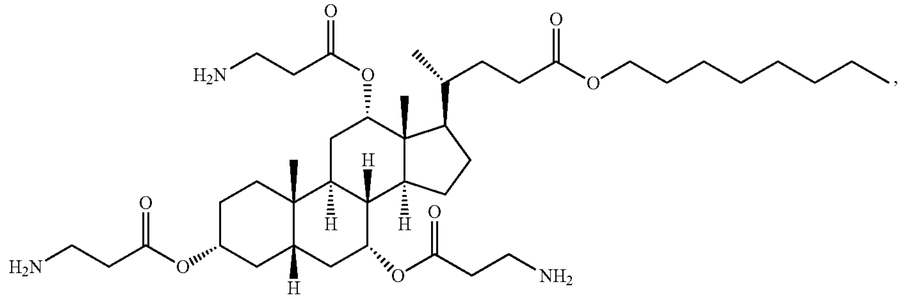
(CSA-90)
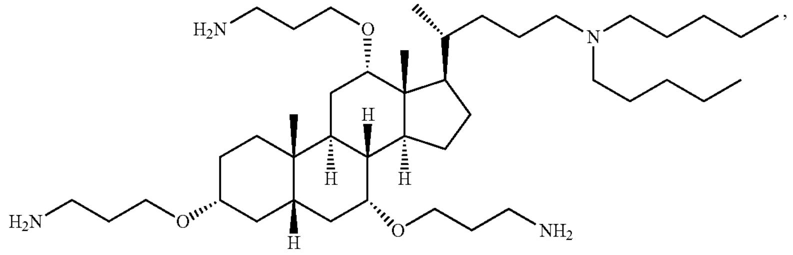
(CSA-135)
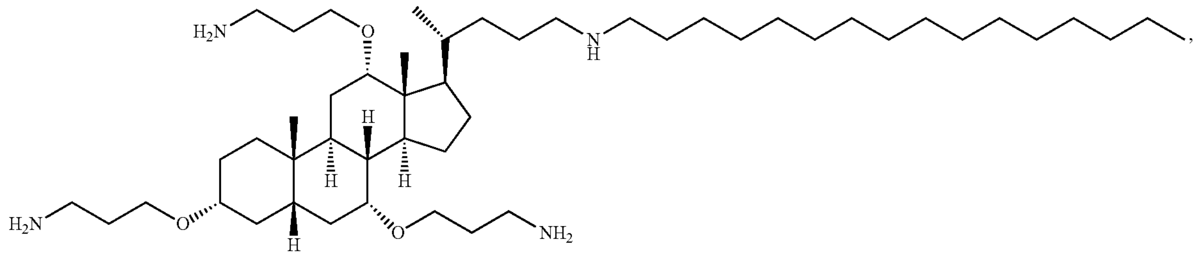
(CSA-131)
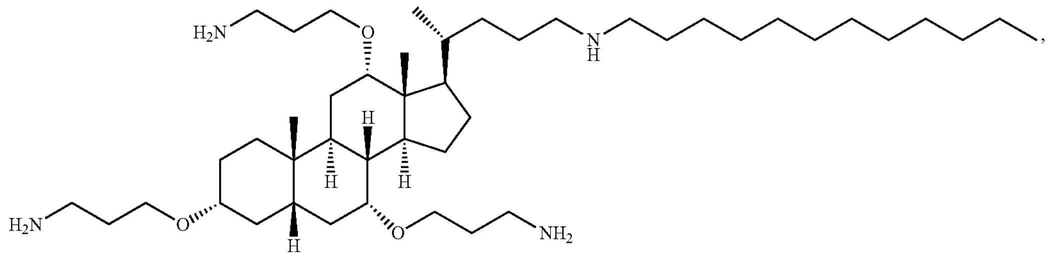

-continued
(CSA-134)
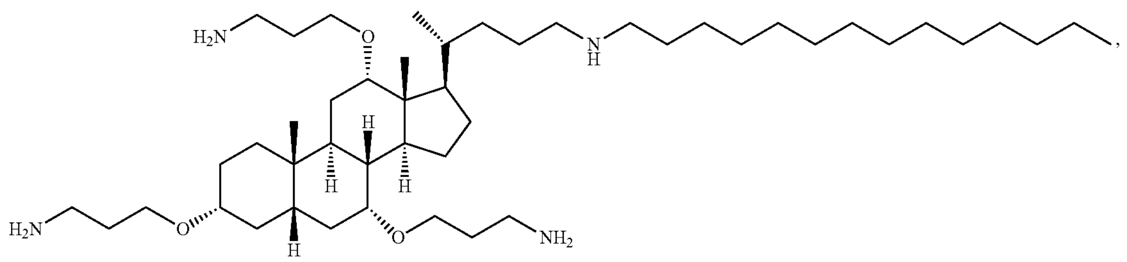
(CSA-136)
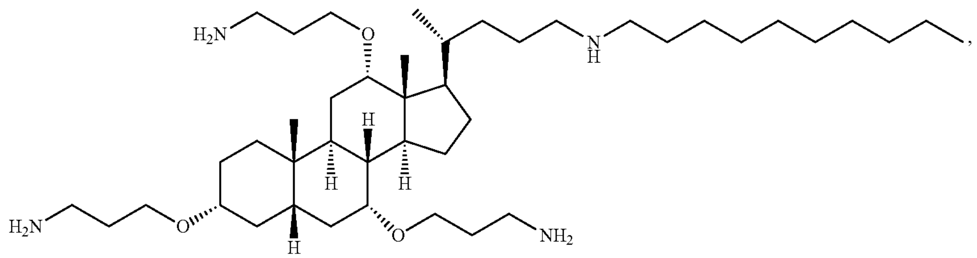
(CSA-137)
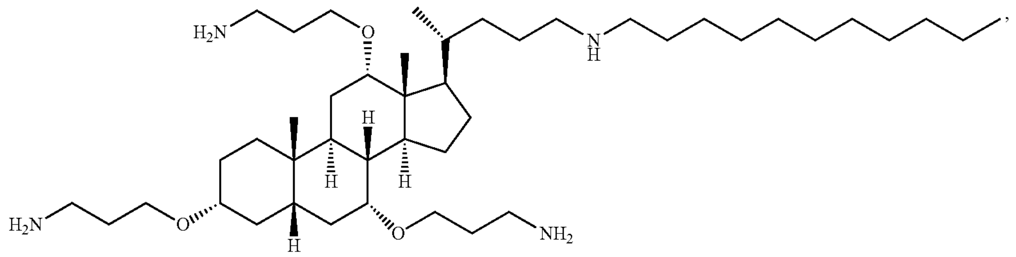
(CSA-138)
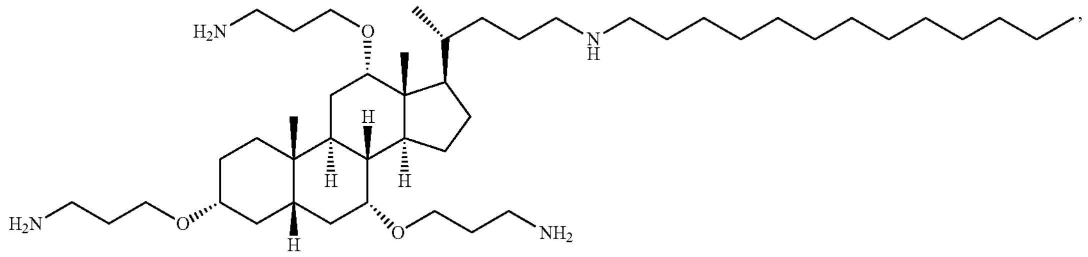
(CSA-142)
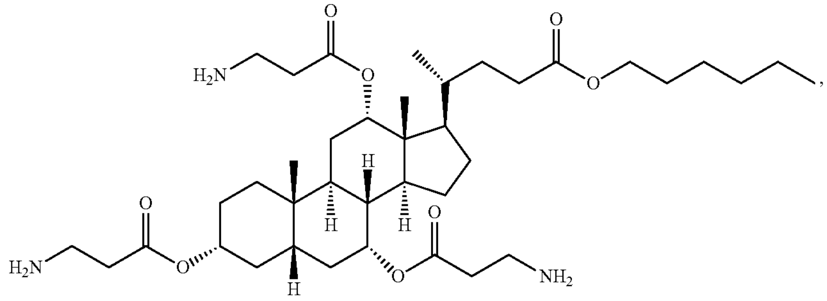

-continued (CSA-144)

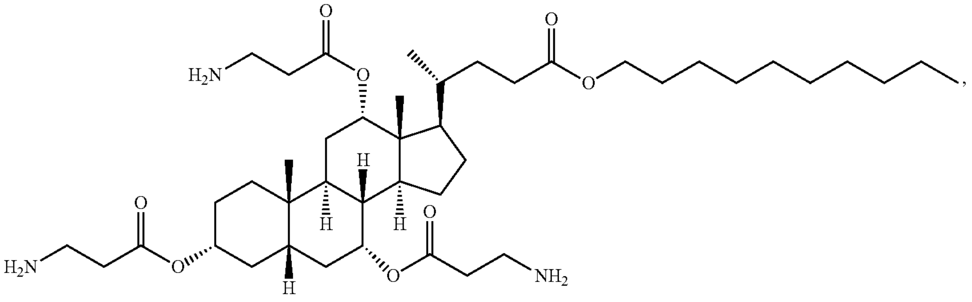

(CSA-145)

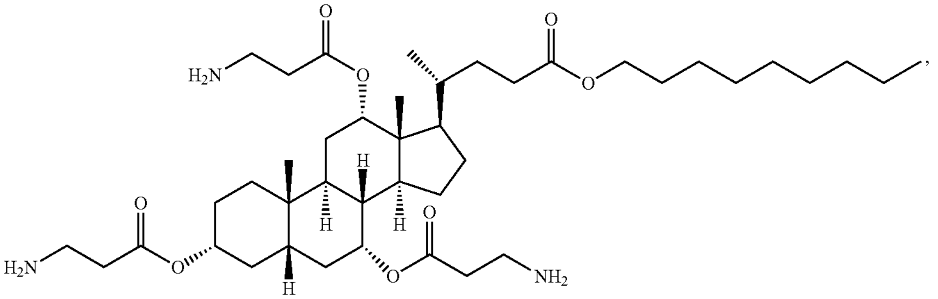

(CSA-146)

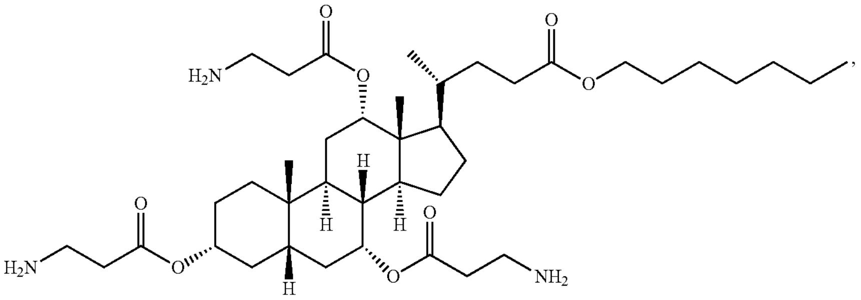

and pharmaceutically acceptable salts thereof.

8. The method of claim 1, wherein the pharmaceutically acceptable salt is a hydrochloride salt selected from a mono-hydrochloride salt, a di-hydrochloride salt, a tri-hydrochloride salt, or a tetra-hydrochloride salt.

9. The method of claim 1, wherein the patient is a mammal.

10. The method of claim 9, wherein the mammal is a human.

11. A method of treating a patient having a lung infection with a cationic steroidal antimicrobial (CSA), comprising:

administering via inhalation into a lung of the patient having the lung infection a therapeutically or prophylactically effective amount of the CSA, which provides antimicrobial activity to treat the lung infection, wherein the CSA is of Formula IB having the following structure, or a pharmaceutically acceptable salt thereof:

(IB)

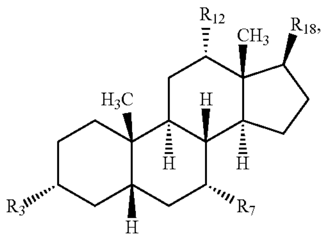

wherein, $R_3$, $R_7$, and $R_{12}$ are independently selected from the group consisting of substituted or unsubstituted aminoalkyloxy and substituted or unsubstituted aminoalkylcarboxyl; and $R_{18}$ is selected from the group consisting of substituted or unsubstituted alkylaminoalkyl; substituted or unsubstituted alkyloxycarbonylalkyl; substituted or unsubstituted alkylcarbonyloxyalkyl; substituted or unsubstituted di(alkyl)-aminoalkyl; substituted or unsubstituted alkylcarboxyalkyl; and substituted or unsubstituted hydroxyalkyl, wherein the CSA is anti-pathogenic with the proviso that the CSA is not CSA-13.

12. The method of claim 11, wherein the lung infection is a bacterial lung infection.

13. The method of claim 11, wherein the lung infection is drug- and/or antibiotic-resistant, and the CSA provides antimicrobial activity against antibiotic-resistant bacteria in the patient's lung.

14. The method of claim 11, wherein the lung infection is tobramycin-resistant, vancomycin-resistant, or methicillin-resistant, and the CSA provides antimicrobial activity against at least one of tobramycin-resistant bacteria, vancomycin-resistant bacteria, or methicillin-resistant bacteria.

15. The method of claim 11, wherein the lung infection is a chronic lung infection, and the CSA provides antimicrobial activity against microbes present in the patient's lung.

16. The method of claim 11, wherein the lung infection is an infection by at least one microbe selected from *Staphylococcus aureus, Haemophilus influenzae, Pseudomonas aeruginosa, Burkholderia cepacia, Aspergillus fumigatus, Aspergillus flavus, Aspergillus nidulans, Aspergillus terreus, Scedosporium apiospermum, Scedosporium prolificans, Candida albicans, Exophiala dermatitidis, Penicillium emersonii*, or *Acrophialophora fusispora* pathogens, and the CSA provides antimicrobial activity against the at least one microbe.

17. The method of claim 11, wherein the patient has allergic broncho-pulmonary aspergillosis, and the CSA provides antimicrobial activity against aspergillosis.

18. The method of claim 11, wherein the lung infection has resulted in the formation of a biofilm in the patient's lung, and wherein the CSA is effective in breaking up the biofilm.

19. The method of claim 11, further comprising administering, in addition to the CSA, at least one additional anti-pathogenic substance, such that at least two anti-pathogenic substances are administered.

20. The method of claim 19, wherein the administration of the at least two different anti-pathogenic substances is concurrent or sequential.

21. The method of claim 19, wherein the at least two different anti-pathogenic substances are at least two different types of CSAs administered via inhalation by the patient into the lung having the lung infection.

22. The method of claim 19, wherein a first anti-pathogenic substance is the CSA and a second anti-pathogenic substance is a non-CSA antimicrobial.

23. The method of claim 22, wherein the second anti-pathogenic substance is an antimicrobial selected from the group consisting of an aminoglycoside, an ansamycin, a carbacephem, a carbapenem, a cephalosporin, a glycopeptide, a lincosamide, a lipopeptide, a macrolide, monobactam, a nitrofuran, an oxazolidonone, a penicillin, a polypeptide, a quinolone, a sulfonamide, and a tetracycline.

24. The method of claim 22, wherein the second anti-pathogenic substance is selected from the group consisting of tobramycin, colistin, aztreonam, ciprofloxacin, azithromycin, erythromycin, and vancomycin.

25. The method of claim 22, wherein the second anti-pathogenic substance is an antifungal or an antiviral.

26. A method of treating a patient having lung inflammation with a cationic steroidal antimicrobial (CSA), comprising:

administering via inhalation into a lung of the patient having the lung inflammation a therapeutically or prophylactically effective amount of the CSA to treat the lung inflammation, wherein the CSA modulates gene expression relating to inflammation, wherein the CSA is of Formula IB having the following structure, or a pharmaceutically acceptable salt thereof:

(IB)

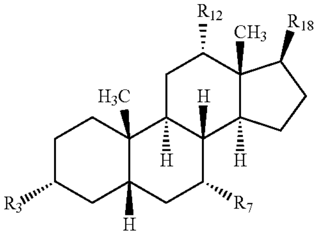

wherein, $R_3$, $R_7$, and $R_{12}$ are independently selected from the group consisting of substituted or unsubstituted aminoalkyloxy and substituted or unsubstituted aminoalkylcarboxyl; and $R_{18}$ is selected from the group consisting of substituted or unsubstituted alkylaminoalkyl; substituted or unsubstituted alkyloxycarbonylalkyl; substituted or unsubstituted alkylcarbonyloxyalkyl; substituted or unsubstituted di(alkyl)-aminoalkyl; substituted or unsubstituted alkylcarboxyalkyl; and substituted or unsubstituted hydroxyalkyl, with the proviso that the CSA is not CSA-13.

27. The method of claim 26, wherein the patient has one or more of cystic fibrosis, allergic broncho-pulmonary aspergillosis, or chronic obstructive pulmonary disease.

28. The method of claim 27, further comprising administering a medication that loosens secretions, wherein the medication that loosens secretions is dornase alfa, a deoxyribonuclease enzyme, saline, or hypotonic saline and the secretions comprise mucus or sputum.

29. The method of claim 26, wherein the CSA reduces lung inflammation mediated by a tumor necrosis factor.

30. The method of claim 26, wherein the CSA reduces lung scarring.

31. The method of claim 26, the method comprising administering at least two different therapeutic substances via inhalation by the patient into the lung having the lung inflammation.

32. The method of claim 26, wherein a first therapeutic substance is the CSA and a second therapeutic substance is a non-CSA therapeutic substance.

33. The method of claim 32, wherein the second therapeutic substance is an antimicrobial.

34. The method of claim 33, wherein the lung inflammation results from a lung infection caused by at least one of a bacterium, virus, or fungus.

35. The method of claim 26, wherein the lung inflammation results from a bacterial lung infection that is drug-resistant and/or antibiotic-resistant.

36. The method of claim 26, wherein the lung inflammation results from a bacterial lung infection that is tobramycin-resistant, vancomycin-resistant, or methicillin-resistant.

37. The method of claim 26, wherein the lung inflammation results from a chronic lung infection.

38. The method of claim 26, wherein the lung inflammation results from an infection by one or more of *Staphylo-*

*coccus, Haemophilus, Pseudomonas, Burkholderia, Aspergillus, Scedosporium, Candida, Exophiala, Penicillium*, or *Acrophialophora* pathogens.

* * * * *